(12) United States Patent
Smith et al.

(10) Patent No.: US 10,967,124 B2
(45) Date of Patent: Apr. 6, 2021

(54) INFUSION PUMPS

(71) Applicant: MEDTRONIC MINIMED, INC., Northridge, CA (US)

(72) Inventors: Roger E. Smith, Ivins, UT (US); Carla Mann Woods, Beverly Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 16/028,280

(22) Filed: Jul. 5, 2018

(65) Prior Publication Data

US 2018/0318502 A1 Nov. 8, 2018

Related U.S. Application Data

(63) Continuation of application No. 14/537,268, filed on Nov. 10, 2014, now Pat. No. 10,029,045, which is a continuation of application No. 13/300,574, filed on Nov. 19, 2011, now Pat. No. 8,905,972.

(60) Provisional application No. 61/415,830, filed on Nov. 20, 2010, provisional application No. 61/487,705, filed on May 18, 2011.

(51) Int. Cl.
*A61M 5/158* (2006.01)
*A61M 5/142* (2006.01)
*A61M 5/14* (2006.01)
*A61M 5/168* (2006.01)

(52) U.S. Cl.
CPC ............ *A61M 5/158* (2013.01); *A61M 5/142* (2013.01); *A61M 5/1413* (2013.01); *A61M 5/14244* (2013.01); *A61M 5/14248* (2013.01); *A61M 2005/14252* (2013.01); *A61M 2005/14268* (2013.01); *A61M 2005/1581* (2013.01); *A61M 2005/1585* (2013.01); *A61M 2005/16863* (2013.01); *A61M 2205/8256* (2013.01); *A61M 2209/01* (2013.01); *Y10T 29/49826* (2015.01)

(58) Field of Classification Search
CPC ......... A61M 2005/14252; A61M 2005/14268; A61M 2005/1581; A61M 2005/1585; A61M 2005/16863; A61M 2205/8256; A61M 2209/01; A61M 5/1413; A61M 5/142; A61M 5/14244; A61M 5/14248; A61M 5/158; Y10T 29/49826
USPC ...................................................... 604/506
See application file for complete search history.

(56) References Cited

U.S. PATENT DOCUMENTS

| 1,771,219 A | 7/1930 | Hein |
| 2,627,270 A | 2/1953 | Glass |

(Continued)

FOREIGN PATENT DOCUMENTS

| CA | 2406026 | 10/2002 |
| CA | 2741716 | 9/2003 |

(Continued)

OTHER PUBLICATIONS

U.S. Appl. No. 12/890,135, filed Sep. 24, 2010, US-2012/0078216 A1 U.S. Pat. No. 8,915,879, Infusion Pumps.

(Continued)

*Primary Examiner* — Jason E Flick
(74) *Attorney, Agent, or Firm* — Cantor Colburn LLP

(57) ABSTRACT

Ambulatory infusion pumps, pump assemblies, and baseplate assemblies, including cartridges, baseplates, cannulas, inserters, and related components and batteries therefor, as well as component combinations and related methods.

15 Claims, 12 Drawing Sheets

(56) References Cited

U.S. PATENT DOCUMENTS

| | | |
|---|---|---|
| 3,662,753 A | 5/1972 | Tassell |
| 3,701,345 A | 10/1972 | Heilman et al. |
| 4,116,240 A | 9/1978 | Guiney |
| 4,206,764 A | 6/1980 | Williams |
| 4,379,453 A | 4/1983 | Baron |
| 4,529,401 A | 7/1985 | Leslie et al. |
| 4,731,058 A | 3/1988 | Doan |
| 4,767,378 A | 8/1988 | Obermann |
| 4,886,499 A | 12/1989 | Cirelli et al. |
| 4,985,015 A | 1/1991 | Obermann et al. |
| 5,244,461 A | 9/1993 | Derlein |
| 5,281,111 A | 1/1994 | Plambeck et al. |
| 5,355,067 A | 10/1994 | Tabuchi |
| 5,364,242 A | 11/1994 | Olsen |
| 5,364,510 A | 11/1994 | Carpio |
| 5,378,126 A | 1/1995 | Abrahamson et al. |
| 5,380,314 A | 1/1995 | Herweck et al. |
| 5,505,709 A | 4/1996 | Funderburk et al. |
| 5,531,697 A | 7/1996 | Olsen et al. |
| 5,549,583 A | 8/1996 | Sanford et al. |
| 5,586,868 A | 12/1996 | Lawless et al. |
| 5,665,065 A | 9/1997 | Colman et al. |
| 5,695,473 A | 12/1997 | Olsen |
| 5,816,779 A | 10/1998 | Lawless et al. |
| 5,858,001 A | 1/1999 | Tsals et al. |
| 5,935,106 A | 8/1999 | Olsen |
| 5,954,696 A | 9/1999 | Ryan |
| 5,984,894 A | 11/1999 | Poulsen et al. |
| 6,033,377 A | 3/2000 | Rasmussen et al. |
| 6,224,577 B1 | 5/2001 | Dedola et al. |
| 6,248,093 B1 | 6/2001 | Moberg |
| 6,296,907 B1 | 10/2001 | Viksne |
| 6,362,591 B1 | 3/2002 | Moberg |
| 6,458,102 B1 | 10/2002 | Mann et al. |
| 6,461,331 B1 | 10/2002 | Van Antwerp |
| 6,482,186 B1 | 11/2002 | Douglas et al. |
| 6,520,930 B2 | 2/2003 | Critchlow et al. |
| 6,537,251 B2 | 3/2003 | Klitmose |
| 6,585,695 B1 | 7/2003 | Adair et al. |
| 6,585,698 B1 | 7/2003 | Packman et al. |
| 6,629,949 B1 | 10/2003 | Douglas |
| 6,641,566 B2 | 11/2003 | Douglas et al. |
| 6,656,158 B2 | 12/2003 | Mahoney et al. |
| 6,656,159 B2 | 12/2003 | Flaherty |
| 6,659,980 B2 | 12/2003 | Moberg et al. |
| 6,692,457 B2 | 2/2004 | Flaherty |
| 6,699,218 B2 | 3/2004 | Flaherty et al. |
| 6,723,072 B2 | 4/2004 | Flaherty et al. |
| 6,736,796 B2 | 5/2004 | Shekalim |
| 6,749,587 B2 | 6/2004 | Flaherty |
| 6,752,787 B1 | 6/2004 | Causey et al. |
| 6,768,425 B2 | 7/2004 | Flaherty et al. |
| 6,800,071 B1 | 10/2004 | McConnell et al. |
| 6,817,990 B2 | 11/2004 | Yap et al. |
| 6,830,558 B2 | 12/2004 | Flaherty et al. |
| 6,852,104 B2 | 2/2005 | Blomquist |
| 6,902,207 B2 | 6/2005 | Lickliter |
| 6,937,955 B2 | 8/2005 | Barnes |
| 6,939,324 B2 | 9/2005 | Gonnelli et al. |
| 7,029,455 B2 | 4/2006 | Flaherty |
| 7,033,338 B2 | 4/2006 | Vilks et al. |
| 7,063,684 B2 | 6/2006 | Moberg |
| 7,137,964 B2 | 11/2006 | Flaherty |
| 7,179,226 B2 | 2/2007 | Crothall et al. |
| 7,193,521 B2 | 3/2007 | Moberg et al. |
| 7,214,207 B2 | 5/2007 | Lynch et al. |
| 7,250,037 B2 | 7/2007 | Shermer et al. |
| 7,303,543 B1 | 12/2007 | Maule et al. |
| 7,306,578 B2 | 12/2007 | Gray et al. |
| 7,311,693 B2 | 12/2007 | Shekalim |
| 7,390,314 B2 | 6/2008 | Stutz, Jr. et al. |
| 7,455,663 B2 | 11/2008 | Bikovsky |
| 7,481,792 B2 | 1/2009 | Gonnelli et al. |
| 7,510,544 B2 | 3/2009 | Vilks et al. |
| 7,534,226 B2 | 5/2009 | Mernoe et al. |
| 7,569,050 B2 | 8/2009 | Moberg et al. |
| 7,621,893 B2 | 11/2009 | Moberg et al. |
| 7,632,247 B2 | 12/2009 | Adams |
| 7,641,628 B2 | 1/2010 | Daoud et al. |
| 7,641,649 B2 | 1/2010 | Moberg et al. |
| 7,713,258 B2 | 5/2010 | Adams et al. |
| 7,713,262 B2 | 5/2010 | Adams et al. |
| 7,726,955 B2 | 6/2010 | Ryser et al. |
| 7,794,434 B2 | 9/2010 | Mounce et al. |
| 7,806,868 B2 | 10/2010 | De Polo et al. |
| 8,282,366 B2 | 10/2012 | Hilber et al. |
| 8,382,700 B2 | 2/2013 | Straessler et al. |
| 8,414,532 B2 | 4/2013 | Brandt et al. |
| 8,430,849 B2 | 4/2013 | Smith et al. |
| 8,465,460 B2 | 6/2013 | Yodfat et al. |
| 8,568,361 B2 * | 10/2013 | Yodfat .............. A61M 5/16854 604/155 |
| 8,777,901 B2 | 7/2014 | Smith et al. |
| 8,905,972 B2 | 12/2014 | Smith et al. |
| 8,915,879 B2 | 12/2014 | Smith et al. |
| 8,957,674 B2 | 2/2015 | Genoud et al. |
| 9,216,249 B2 | 12/2015 | Smith et al. |
| 9,222,470 B2 | 12/2015 | Genoud et al. |
| 9,302,285 B2 | 4/2016 | Marbet et al. |
| 9,308,320 B2 | 4/2016 | Smith et al. |
| 9,320,849 B2 | 4/2016 | Smith et al. |
| 9,381,300 B2 | 7/2016 | Smith et al. |
| 9,498,573 B2 | 11/2016 | Smith et al. |
| 9,750,875 B2 | 9/2017 | Smith et al. |
| 10,029,045 B2 | 7/2018 | Smith et al. |
| 10,342,918 B2 | 7/2019 | Politis et al. |
| 10,398,853 B2 | 9/2019 | Huwiler et al. |
| 2001/0034502 A1 | 10/2001 | Moberg et al. |
| 2001/0041869 A1 | 11/2001 | Causey, III et al. |
| 2001/0053887 A1 | 12/2001 | Douglas et al. |
| 2002/0040208 A1 | 4/2002 | Flaherty et al. |
| 2002/0077598 A1 | 6/2002 | Yap et al. |
| 2002/0091358 A1 | 7/2002 | Klitmose |
| 2002/0123740 A1 | 9/2002 | Flaherty et al. |
| 2002/0151855 A1 | 10/2002 | Douglas et al. |
| 2002/0173748 A1 | 11/2002 | McConnell et al. |
| 2002/0173769 A1 | 11/2002 | Gray et al. |
| 2002/0183616 A1 | 12/2002 | Toews et al. |
| 2003/0040700 A1 | 2/2003 | Hickle et al. |
| 2003/0055380 A1 | 3/2003 | Flaherty |
| 2003/0073952 A1 | 4/2003 | Flaherty et al. |
| 2003/0100863 A1 | 5/2003 | Shekalim |
| 2003/0125672 A1 | 7/2003 | Adair et al. |
| 2003/0135159 A1 | 7/2003 | Daily et al. |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0167036 A1 | 9/2003 | Flaherty |
| 2003/0167039 A1 | 9/2003 | Moberg |
| 2003/0199085 A1 | 10/2003 | Berger et al. |
| 2003/0199824 A1 | 10/2003 | Mahoney et al. |
| 2003/0199825 A1 | 10/2003 | Flaherty |
| 2003/0216683 A1 | 11/2003 | Shekalim |
| 2003/0233069 A1 | 12/2003 | Gillespie, Jr. et al. |
| 2004/0003493 A1 | 1/2004 | Adair et al. |
| 2004/0078028 A1 | 4/2004 | Flaherty et al. |
| 2004/0085215 A1 | 5/2004 | Moberg et al. |
| 2004/0092865 A1 | 5/2004 | Flaherty et al. |
| 2004/0092873 A1 | 5/2004 | Moberg |
| 2004/0092878 A1 | 5/2004 | Flaherty |
| 2004/0127844 A1 | 7/2004 | Flaherty |
| 2004/0133166 A1 | 7/2004 | Moberg et al. |
| 2004/0138612 A1 | 7/2004 | Shermer et al. |
| 2004/0153032 A1 | 8/2004 | Garribotto et al. |
| 2004/0176727 A1 | 9/2004 | Shekalim |
| 2004/0220551 A1 | 11/2004 | Flaherty et al. |
| 2004/0231667 A1 | 11/2004 | Horton et al. |
| 2004/0235446 A1 | 11/2004 | Flaherty et al. |
| 2004/0243065 A1 | 12/2004 | McConnell et al. |
| 2004/0254533 A1 | 12/2004 | Schriver et al. |
| 2005/0020980 A1 | 1/2005 | Inoue et al. |
| 2005/0021000 A1 | 1/2005 | Adair et al. |
| 2005/0021005 A1 | 1/2005 | Flaherty et al. |

(56) References Cited

U.S. PATENT DOCUMENTS

| | | |
|---|---|---|
| 2005/0022274 A1 | 1/2005 | Campbell et al. |
| 2005/0065472 A1 | 3/2005 | Cindrich et al. |
| 2005/0090808 A1 | 4/2005 | Malave et al. |
| 2005/0148938 A1 | 7/2005 | Blomquist |
| 2005/0171476 A1 | 8/2005 | Judson et al. |
| 2005/0182366 A1 | 8/2005 | Vogt et al. |
| 2005/0197626 A1 | 9/2005 | Moberg et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2006/0074381 A1 | 4/2006 | Malave et al. |
| 2006/0095014 A1 | 5/2006 | Ethelfeld |
| 2006/0178633 A1 | 8/2006 | Garibotto et al. |
| 2006/0184154 A1 | 8/2006 | Moberg et al. |
| 2006/0189939 A1 | 8/2006 | Gonnelli et al. |
| 2006/0200112 A1 | 9/2006 | Paul |
| 2006/0206054 A1 | 9/2006 | Shekalim |
| 2006/0282290 A1 | 12/2006 | Flaherty et al. |
| 2007/0021733 A1 | 1/2007 | Hansen et al. |
| 2007/0049870 A1 | 3/2007 | Gray et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0100283 A1 | 5/2007 | Causey et al. |
| 2007/0118405 A1 | 5/2007 | Campbell et al. |
| 2007/0123819 A1 | 5/2007 | Mernoe et al. |
| 2007/0149861 A1 | 6/2007 | Crothall et al. |
| 2007/0149926 A1 | 6/2007 | Moberg et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173762 A1 | 7/2007 | Estes et al. |
| 2007/0179444 A1 | 8/2007 | Causey et al. |
| 2007/0191772 A1 | 8/2007 | Wojcik |
| 2007/0204603 A1 | 9/2007 | Jacobs et al. |
| 2007/0219480 A1 | 9/2007 | Kamen et al. |
| 2007/0228071 A1 | 10/2007 | Kamen et al. |
| 2007/0276329 A1 | 11/2007 | Mernoe |
| 2007/0282269 A1 | 12/2007 | Carter et al. |
| 2007/0287960 A1 | 12/2007 | Adams et al. |
| 2007/0293826 A1 | 12/2007 | Wall et al. |
| 2007/0299397 A1 | 12/2007 | Alferness et al. |
| 2007/0299398 A1 | 12/2007 | Alferness et al. |
| 2007/0299399 A1 | 12/2007 | Alferness et al. |
| 2007/0299400 A1 | 12/2007 | Alferness et al. |
| 2007/0299401 A1 | 12/2007 | Alferness et al. |
| 2007/0299405 A1 | 12/2007 | Kaufmann et al. |
| 2007/0299408 A1 | 12/2007 | Alferness et al. |
| 2008/0021395 A1 | 1/2008 | Yodfat et al. |
| 2008/0027296 A1 | 1/2008 | Hadvary et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0058718 A1 | 3/2008 | Adams et al. |
| 2008/0097318 A1 | 4/2008 | Adams |
| 2008/0097324 A1 | 4/2008 | Adams et al. |
| 2008/0097381 A1 | 4/2008 | Moberg et al. |
| 2008/0119790 A1 | 5/2008 | Hawkins et al. |
| 2008/0132842 A1 | 6/2008 | Flaherty |
| 2008/0167620 A1 | 7/2008 | Adams et al. |
| 2008/0215006 A1 | 9/2008 | Thorkild |
| 2008/0215015 A1 | 9/2008 | Cindrich et al. |
| 2008/0215035 A1 | 9/2008 | Yodfat et al. |
| 2008/0234630 A1 | 9/2008 | Iddan et al. |
| 2008/0255516 A1 | 10/2008 | Yodfat et al. |
| 2008/0269687 A1 | 10/2008 | Chong et al. |
| 2008/0281270 A1 | 11/2008 | Cross et al. |
| 2008/0294094 A1 | 11/2008 | Mhatre et al. |
| 2008/0294142 A1 | 11/2008 | Patel et al. |
| 2008/0312512 A1 | 12/2008 | Brukalo et al. |
| 2008/0312584 A1 | 12/2008 | Montgomery et al. |
| 2008/0312585 A1 | 12/2008 | Brukalo et al. |
| 2008/0319416 A1 | 12/2008 | Yodfat et al. |
| 2009/0006129 A1 | 1/2009 | Thukral et al. |
| 2009/0030382 A1 | 1/2009 | Brandt et al. |
| 2009/0048563 A1 | 2/2009 | Ethelfeld et al. |
| 2009/0048578 A1 | 2/2009 | Adams et al. |
| 2009/0054866 A1 | 2/2009 | Teisen-Simony et al. |
| 2009/0062747 A1 | 3/2009 | Saul |
| 2009/0062768 A1 | 3/2009 | Saul |
| 2009/0067989 A1* | 3/2009 | Estes ................ A61M 5/14244 415/118 |
| 2009/0069784 A1 | 3/2009 | Estes et al. |
| 2009/0069787 A1 | 3/2009 | Estes et al. |
| 2009/0076451 A1 | 3/2009 | Teisen-Simony et al. |
| 2009/0076453 A1 | 3/2009 | Mejlhede et al. |
| 2009/0088682 A1 | 4/2009 | Cross et al. |
| 2009/0088689 A1 | 4/2009 | Carter |
| 2009/0088690 A1 | 4/2009 | Carter et al. |
| 2009/0088691 A1 | 4/2009 | Carter et al. |
| 2009/0088692 A1 | 4/2009 | Adams et al. |
| 2009/0088693 A1 | 4/2009 | Carter |
| 2009/0088694 A1 | 4/2009 | Carter et al. |
| 2009/0099521 A1 | 4/2009 | Gravesen et al. |
| 2009/0099523 A1 | 4/2009 | Grant et al. |
| 2009/0131860 A1 | 5/2009 | Nielsen |
| 2009/0143735 A1 | 6/2009 | De Polo et al. |
| 2009/0156989 A1 | 6/2009 | Carter et al. |
| 2009/0163865 A1 | 6/2009 | Hines et al. |
| 2009/0163866 A1 | 6/2009 | Hines et al. |
| 2009/0166978 A1 | 7/2009 | Hoffmann et al. |
| 2009/0182277 A1 | 7/2009 | Carter |
| 2009/0192471 A1 | 7/2009 | Carter et al. |
| 2009/0198186 A1 | 8/2009 | Mernoe et al. |
| 2009/0198215 A1* | 8/2009 | Chong ................ A61M 5/1413 604/506 |
| 2009/0221971 A1 | 9/2009 | Mejlhede et al. |
| 2009/0240240 A1 | 9/2009 | Hines et al. |
| 2009/0254037 A1 | 10/2009 | Bryant, Jr. et al. |
| 2009/0254041 A1 | 10/2009 | Krag et al. |
| 2009/0259176 A1 | 10/2009 | Yairi |
| 2009/0320569 A1 | 12/2009 | Haslem et al. |
| 2009/0326453 A1 | 12/2009 | Adams et al. |
| 2009/0326454 A1 | 12/2009 | Cross et al. |
| 2009/0326455 A1 | 12/2009 | Carter |
| 2009/0326456 A1 | 12/2009 | Cross et al. |
| 2009/0326472 A1 | 12/2009 | Carter et al. |
| 2010/0049128 A1 | 2/2010 | McKenzie et al. |
| 2010/0069848 A1 | 3/2010 | Alferness et al. |
| 2010/0100056 A1 | 4/2010 | Cawthon et al. |
| 2010/0137695 A1 | 6/2010 | Yodfat et al. |
| 2010/0198060 A1 | 8/2010 | Fago et al. |
| 2010/0217105 A1 | 8/2010 | Yodfat et al. |
| 2010/0241063 A1 | 9/2010 | Straessler et al. |
| 2010/0262078 A1 | 10/2010 | Blomquist |
| 2011/0034883 A1 | 2/2011 | Gyrn et al. |
| 2011/0144615 A1 | 6/2011 | Haenggi et al. |
| 2011/0196337 A1 | 8/2011 | Brandt et al. |
| 2011/0224603 A1 | 9/2011 | Richter |
| 2011/0238015 A1 | 9/2011 | Matusch |
| 2012/0022354 A1 | 1/2012 | Beyer et al. |
| 2012/0022452 A1 | 1/2012 | Welsch et al. |
| 2012/0046651 A1 | 2/2012 | Beyer et al. |
| 2012/0053522 A1 | 3/2012 | Yodfat et al. |
| 2012/0078170 A1 | 3/2012 | Smith et al. |
| 2012/0078181 A1 | 3/2012 | Smith et al. |
| 2012/0078182 A1 | 3/2012 | Smith et al. |
| 2012/0078183 A1 | 3/2012 | Smith et al. |
| 2012/0078184 A1 | 3/2012 | Smith et al. |
| 2012/0078185 A1 | 3/2012 | Smith et al. |
| 2012/0078216 A1 | 3/2012 | Smith et al. |
| 2012/0078217 A1 | 3/2012 | Smith et al. |
| 2012/0078222 A1 | 3/2012 | Smith et al. |
| 2012/0116311 A1 | 5/2012 | Bruggemann et al. |
| 2012/0184907 A1 | 7/2012 | Smith et al. |
| 2012/0184909 A1 | 7/2012 | Gyrn |
| 2012/0191043 A1 | 7/2012 | Yodfat et al. |
| 2012/0215163 A1 | 8/2012 | Hanson et al. |
| 2012/0245515 A1 | 9/2012 | Calasso et al. |
| 2012/0302844 A1 | 11/2012 | Schnidrig et al. |
| 2013/0310801 A1 | 11/2013 | Yodfat et al. |
| 2014/0231549 A1 | 8/2014 | Thiemer et al. |

(56) References Cited

U.S. PATENT DOCUMENTS

| | | |
|---|---|---|
| 2014/0296786 A1 | 10/2014 | Servansky et al. |
| 2015/0011939 A1 | 1/2015 | Marbet et al. |
| 2015/0073386 A1 | 3/2015 | Smith et al. |
| 2015/0126934 A1 | 5/2015 | Chong et al. |
| 2015/0133855 A1 | 5/2015 | Smith et al. |
| 2016/0030663 A1 | 2/2016 | Adaniya et al. |
| 2016/0058474 A1 | 3/2016 | Peterson et al. |
| 2016/0089491 A1 | 3/2016 | Smith |
| 2016/0184512 A1 | 6/2016 | Marbet et al. |
| 2016/0235913 A1 | 8/2016 | Smith et al. |
| 2017/0232191 A1 | 8/2017 | Smith et al. |
| 2018/0185572 A1 | 7/2018 | Smith et al. |
| 2018/0318502 A1 | 11/2018 | Smith et al. |
| 2019/0015585 A1 | 1/2019 | Smith |
| 2019/0076599 A1 | 3/2019 | Smith |
| 2019/0321543 A1 | 10/2019 | Smith et al. |

FOREIGN PATENT DOCUMENTS

| | | |
|---|---|---|
| CA | 2632995 A1 | 7/2007 |
| CA | 2659616 | 2/2008 |
| CA | 2921304 | 2/2011 |
| CA | 2842951 | 7/2011 |
| CH | 688224 A5 | 6/1997 |
| CN | 101574550 A | 11/2009 |
| CN | 101745163 A | 6/2010 |
| EP | 2324872 A2 | 5/2011 |
| JP | 59-127595 A | 7/1984 |
| JP | S59127595 A | 7/1984 |
| JP | 01-298998 A | 12/1989 |
| JP | 08-168297 A | 6/1996 |
| JP | 2002-078386 A | 3/2002 |
| JP | 2002078386 A | 3/2002 |
| JP | 2008168297 A | 7/2008 |
| JP | 2009030311 A | 2/2009 |
| JP | 2015521948 A | 8/2015 |
| SU | 437871 | 7/1974 |
| WO | 198503007 A1 | 7/1985 |
| WO | WO 9948546 A1 | 9/1999 |
| WO | WO 0025844 A1 | 5/2000 |
| WO | WO 0170307 A1 | 9/2001 |
| WO | WO 020073 A2 | 3/2002 |
| WO | WO 0228455 A1 | 4/2002 |
| WO | WO 0249509 A2 | 6/2002 |
| WO | WO 02094352 A2 | 11/2002 |
| WO | WO 03045302 A2 | 6/2003 |
| WO | WO 03074121 A1 | 9/2003 |
| WO | WO 2004098390 A2 | 11/2004 |
| WO | WO 2005018703 A2 | 3/2005 |
| WO | WO 2005018705 A2 | 3/2005 |
| WO | WO 2005037350 A2 | 4/2005 |
| WO | WO 2005046756 A2 | 5/2005 |
| WO | WO 2005072794 A2 | 8/2005 |
| WO | WO 2005072795 A2 | 8/2005 |
| WO | WO 2006032689 A1 | 3/2006 |
| WO | WO 2006032692 A1 | 3/2006 |
| WO | WO 2006061354 A1 | 6/2006 |
| WO | WO 2006104806 A2 | 10/2006 |
| WO | WO 2006108809 A1 | 10/2006 |
| WO | WO 2007038059 A2 | 4/2007 |
| WO | WO 2007038060 A2 | 4/2007 |
| WO | WO 2007038091 A2 | 4/2007 |
| WO | 2007094833 A1 | 8/2007 |
| WO | 2007140631 A1 | 12/2007 |
| WO | WO 2007142867 A2 | 12/2007 |
| WO | WO 2007142890 A2 | 12/2007 |
| WO | WO 2008040762 A1 | 4/2008 |
| WO | 2008063429 A2 | 5/2008 |
| WO | 2008082126 A | 7/2008 |
| WO | WO 2008078318 A2 | 7/2008 |
| WO | WO 2008103175 A1 | 8/2008 |
| WO | WO 2008122983 A1 | 10/2008 |
| WO | WO 2008139458 A2 | 11/2008 |
| WO | WO 2008139459 A1 | 11/2008 |
| WO | WO 2008139460 A2 | 11/2008 |
| WO | 2009016637 A2 | 2/2009 |
| WO | WO 2009016635 A2 | 2/2009 |
| WO | WO 2009016636 A2 | 2/2009 |
| WO | WO 2009016637 A2 | 2/2009 |
| WO | WO 2009045776 A2 | 4/2009 |
| WO | WO 2009045779 A2 | 4/2009 |
| WO | WO 2009045781 A2 | 4/2009 |
| WO | WO 2009045784 A2 | 4/2009 |
| WO | WO 2009045785 A2 | 4/2009 |
| WO | WO 2009066288 A1 | 5/2009 |
| WO | WO 2009079528 A1 | 6/2009 |
| WO | WO 2009081399 A1 | 7/2009 |
| WO | WO 2009088956 A2 | 7/2009 |
| WO | 2009101130 A1 | 8/2009 |
| WO | WO 2009097292 A2 | 8/2009 |
| WO | WO 2009113060 A2 | 9/2009 |
| WO | WO 2009113075 A1 | 9/2009 |
| WO | WO 2009116045 A1 | 9/2009 |
| WO | WO 2009125398 A2 | 10/2009 |
| WO | WO 2009133557 A2 | 11/2009 |
| WO | WO 2009146080 A2 | 12/2009 |
| WO | WO 2009158651 A2 | 12/2009 |
| WO | WO 2010022069 A2 | 2/2010 |
| WO | WO 2010026580 A2 | 3/2010 |
| WO | WO 2010029054 A2 | 3/2010 |
| WO | WO 2010029551 A2 | 3/2010 |
| WO | WO 2010031424 A1 | 3/2010 |
| WO | 2010051369 A1 | 5/2010 |
| WO | WO 2011022250 A1 | 2/2011 |
| WO | 2011146166 A1 | 11/2011 |
| WO | 2012040528 A1 | 3/2012 |
| WO | 2014116274 A | 7/2014 |
| WO | 2016133789 A2 | 8/2016 |
| WO | 2017135936 A1 | 8/2017 |
| WO | 2017139723 A1 | 8/2017 |

OTHER PUBLICATIONS

U.S. Appl. No. 14/578,996, filed Dec. 22, 2014, US-2015/0133855 A1, Infusion Pumps.
U.S. Appl. No. 12/890,166, filed Sep. 24, 2010, US-2012/0078181 A1 U.S. Pat. No. 9,498,573, Infusion Pumps.
U.S. Appl. No. 12/890,207, filed Sep. 24, 2010, US-2012/0078170 A1 U.S. Pat. No. 8,777,901, Infusion Pumps.
U.S. Appl. No. 12/890,229, filed Sep. 24, 2010, US-2012/0078222 A1 U.S. Pat. No. 9,320,849, Infusion Pumps.
U.S. Appl. No. 12/890,258, filed Sep. 24, 2010, US-2012/0078182 A1 U.S. Pat. No. 9,308,320, Infusion Pumps.
U.S. Appl. No. 12/890,277, filed Sep. 24, 2010, US-2012/0078183 A1 U.S. Pat. No. 8,430,849, Infusion Pumps.
U.S. Appl. No. 12/890,300, filed Sep. 24, 2010, US-2012/0078184 A1 U.S. Pat. No. 9,381,300, Infusion Pumps.
U.S. Appl. No. 12/890,320, filed Sep. 24, 2010, US-2012/0078185 A1 U.S. Pat. No. 9,750,875, Infusion Pumps.
U.S. Appl. No. 12/890,339, filed Sep. 24, 2010, US-2012/0078217 A1 U.S. Pat. No. 9,216,249, Infusion Pumps.
U.S. Appl. No. 13/300,574, filed Nov. 19, 2011, US-2012/0184907 A1 U.S. Pat. No. 8,905,972, Infusion Pumps.
U.S. Appl. No. 14/537,268, filed Nov. 10, 2014, US-2015/0073386 A1 U.S. Pat. No. 10,029,045, Infusion Pumps.
U.S. Appl. No. 10/028,280, filed Jul. 5, 2018 Infusion Pumps.
U.S. Appl. No. 13/475,843, filed May 18, 2012, US-2013/0138078 A1 U.S. Pat. No. 9,114,208, Infusion Pumps and Inserters for Use With Same.
U.S. Appl. No. 14/819,721, filed Aug. 6, 2015, US-2016/0121045 A1, U.S. Pat. No. 9,839,747, Infusion Pumps and Inserters for Use With Same.
U.S. Appl. No. 15/829,899, filed Dec. 2, 2017, US-2018/0185572 A1, Infusion Pumps and Inserters for Use With Same.
U.S. Appl. No. 14/869,906, filed Sep. 29, 2015, US-2016/0089491 A1, Hybrid Ambulatory Infusion Pumps.
U.S. Appl. No. 15/042,093, filed Feb. 11, 2016, US-2016/0235913A1, Ambulatory Infusion Pumps and Reservoir Assemblies for use With Same.

(56) References Cited

OTHER PUBLICATIONS

U.S. Appl. No. 15/430,513, filed Feb. 12, 2017, US-2017/0232191 A1, Ambulatory Infusion Pumps and Assemblies for use With Same.
U.S. Appl. No. 16/038,048, filed Jul. 17, 2018, Ambulatory Infusion Pumps and Assemblies for use With Same.
CareFusion, Alaris SE Pump Directions for Use (2011).
Knee et al., "A novel use of U-500 insulin for continuous subcutaneous insulin infusion in patients with insulin resistance," Endocrine Practice, vol. 9, No. 3, (May 2003).
Medtronic, "The MiniMed, Paradigm Real-Time, Insulin Pump and Continuous Glucose Monitor System, Insulin Pump UserGuide," (2008).
Gnanalingham et al., "Accuracy and reproducibility of low dose insulin administration using pen-injectors and syringes," Arch Dis Child 1998; 79: 59-62.
Novo Nordisk Canada, Inc., "NovoPen4 User Manual English," 2009.
Kristensen et al., "Dose accuracy and durability of a durable insulin pen before and after simulated lifetime use," Current Medical Research and Opinion, Oct. 2011; 27, No. 10: 1877-1883.
Animas Corp., "OneTouch Ping Owner's Booklet," Jul. 2008.
Garget al., "U-500 insulin: why, when and how to use in clinical practice," Diabetes/Metabolism Research and Reviews, Abstract, Nov. 2006, vol. 23, Is. 4, 265-268.
Extended European Search Report; Application No. 20166121.2; dated Jul. 10, 2020; 12 pages.
Jahn et al.; "Comparative Dose Accuracy of Durable and Patch Insulin Infusion Pumps"; Journal of Diabetes Science and Technology; 7(4); pp. 1011-1020; Jul. 2013.
Extended European Search Report; Application No. 19210609.4; dated Jun. 23, 2020; 5 pages.
CN Application No. 201680083837.4; English Translation of Office Action dated Aug. 6, 2020, 11 pages.
European Office Action; Application No. 17706380.7-1122; dated Aug. 18, 2020; 7 pages.
Australian Application 2019284140 Examination Report No. 2; dated Oct. 7, 2020; 4 pages.
JP Patent Application No. 2018-542219 Notice of Reasons for Refusal (translated) dated Dec. 1, 2020, 6 pages.

\* cited by examiner

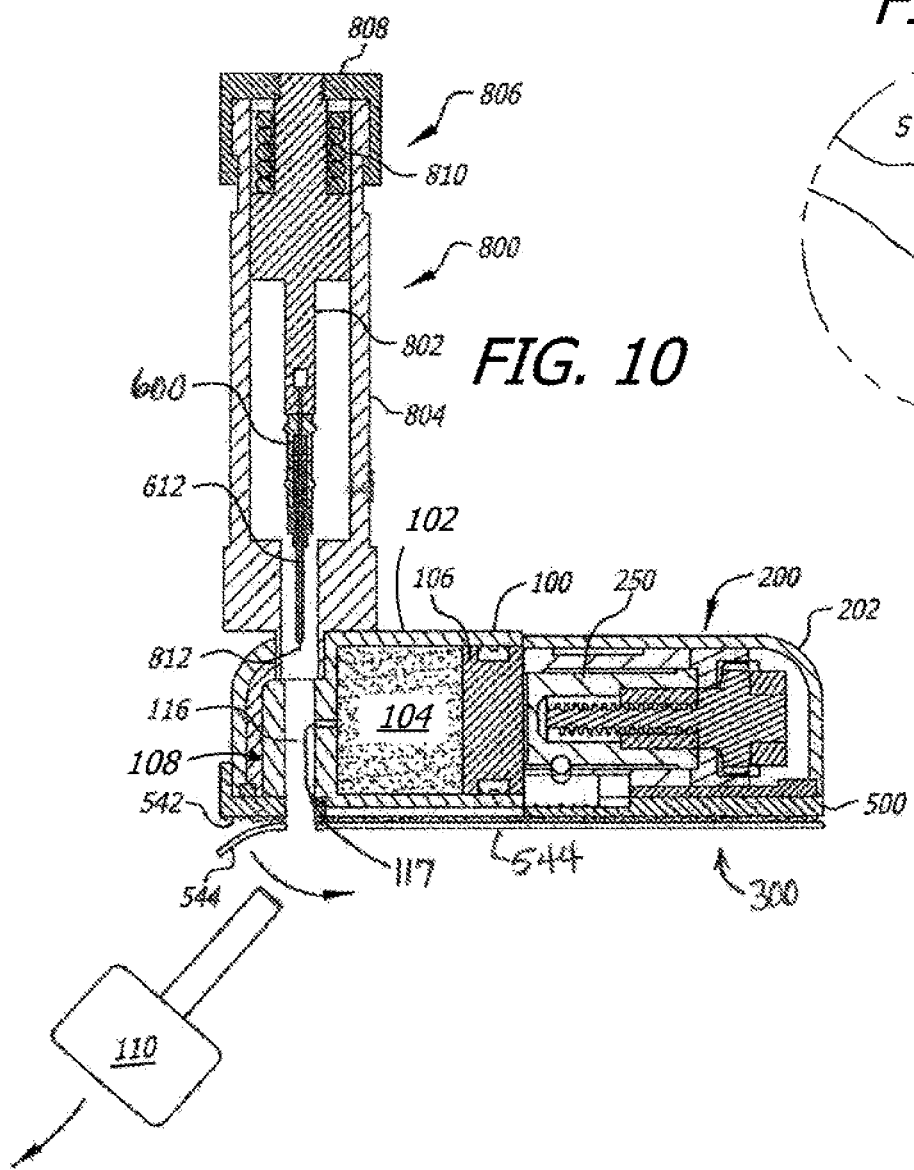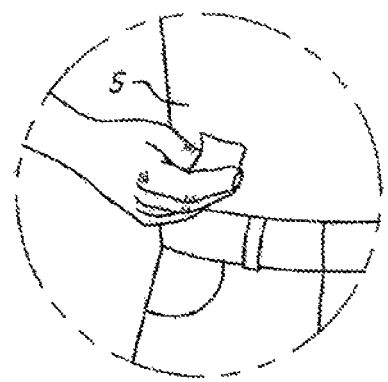

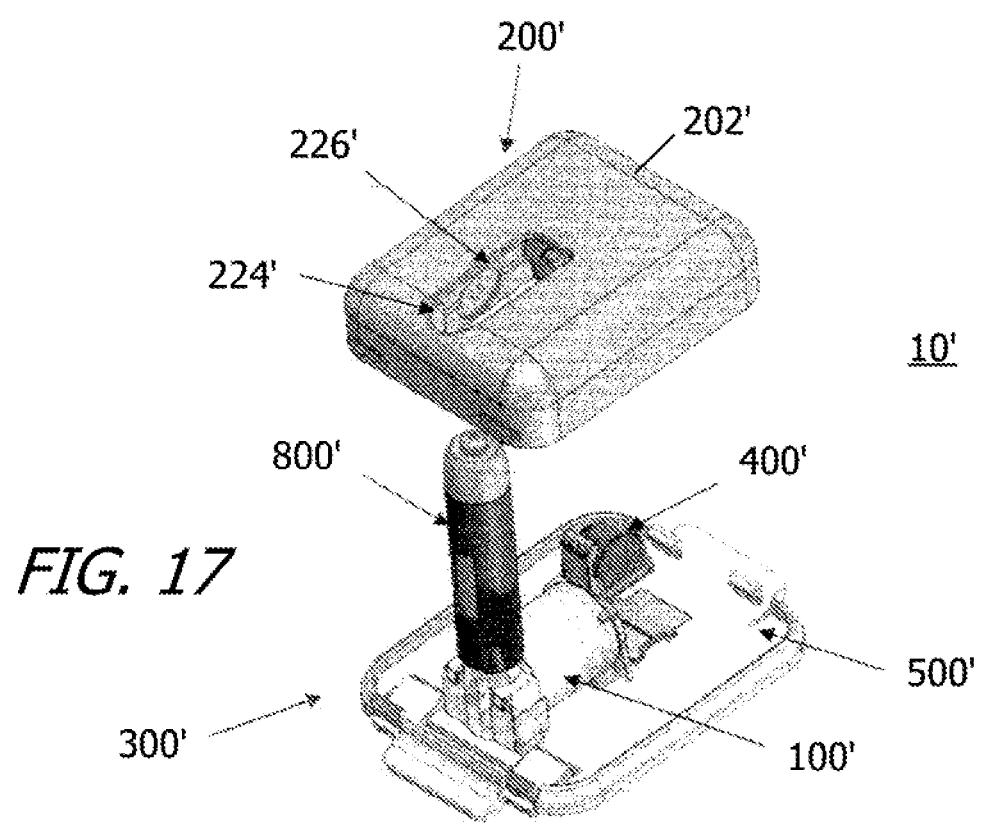

INFUSION PUMPS

CROSS-REFERENCE TO RELATED APPLICATION

This application is a continuation of U.S. application Ser. No. 14/537,268, filed Nov. 10, 2014, which is a continuation of U.S. application Ser. No. 13/300,574, filed Nov. 19, 2011, now U.S. Pat. No. 8,905,972, which claims the benefit of U.S. Provisional Application Ser. No. 61/415,830, filed Nov. 20, 2010 and entitled "Infusion Pumps," and which claims the benefit of U.S. Provisional Application Ser. No. 61/487,705, filed May 18, 2011 and entitled "Infusion Pumps," each of which is incorporated herein by reference in its entirety.

BACKGROUND

1. Field

The present devices and methods relate generally to ambulatory infusion pumps.

2. Description of the Related Art

Ambulatory infusion pumps (also referred to herein simply as "infusion pumps") are relatively small, at least substantially self-contained devices that are used to introduce drugs and other infusible substances (collectively "medicament") into patients' bodies. Some infusion pumps are configured to be worn on a belt or carried in a clothing pocket. Other infusion pumps are configured to be adhered to skin in patch-like fashion. Infusion pumps are advantageous in that they may be used to, for example, subcutaneously introduce (or "infuse") medicament on an ongoing or even continuous basis outside of a clinical environment. Infusion pumps are also advantageous in that they greatly reduce the frequency of subcutaneous access events such as needle-based shots. One example of a medicament that may be introduced by an infusion pump is a liquid formulation of insulin. Other exemplary medicaments that may be introduced by an infusion pump include, but are not limited to, drugs that treat cancers and drugs that suppress the perception of pain.

Many conventional infusion pumps have improved patient health and quality of life. Nevertheless, the present inventors have determined that conventional infusion pumps are susceptible to a wide range of improvements. By way of example, but not limitation, the present inventors have determined that it would be desirable to provide an infusion pump that is smeller, more accurate and/or provides more operational flexibility than conventional infusion pumps.

SUMMARY

A system in accordance with at least one of the present inventions includes an infusion pump assembly and a baseplate assembly. The infusion, pump assembly may include a housing and a rechargeable battery in the housing. The baseplate assembly may include a baseplate and a baseplate energy supply, and may be configured to be attached to the infusion pump housing. Energy from the baseplate power supply may be transferred to the rechargeable battery when the baseplate assembly is attached to the housing.

A method in accordance with at least one of the present inventions includes the step of securing a baseplate assembly with a baseplate energy supply to an infusion pump assembly with a rechargeable battery such that energy from the baseplate energy supply is transferred to the rechargeable battery.

An infusion pump system in accordance with at least one of the present inventions includes an infusion pump assembly with a plunger pusher and a baseplate assembly with a baseplate and a medicament cartridge, including a barrel defining a reservoir and a plunger movable within the barrel, on the baseplate. The infusion pump assembly and the baseplate assembly may be configured to be attached to one another in such a manner that the plunger pusher will be aligned with the plunger.

A baseplate assembly in accordance with at least one of the present inventions includes a baseplate, a medicament cartridge on the baseplate defining a reservoir, a cannula and a cannula inserter.

The features and attendant advantages of the present inventions will become apparent as the inventions become better understood by reference to the following detailed description when considered in conjunction with the accompanying drawings.

BRIEF DESCRIPTION OF THE DRAWINGS

Detailed description of exemplary embodiments will be made with reference to the accompanying drawings.

FIG. 9 is a front view showing a patient's skin being cleaned.

FIG. 10 is a section view showing the pump assembly attached to the exemplary baseplate assembly, including cartridge, a cannula inserter, and cannula, plus a pull before use plug.

FIG. 17 is an exploded perspective view of another exemplary infusion pump system.

DETAILED DESCRIPTION

The following is a detailed description of the best presently known modes of carrying out the inventions. This description is not to be taken in a limiting sense, but is made merely for the purpose of illustrating the general principles of the inventions.

It should also be noted here that the specification describes structures and methods, mainly in the context of cartridge-based infusion pumps, which are especially well-suited for the subcutaneous delivery of very high concentration insulin (e.g., the U-500 insulin discussed below). Nevertheless, it should be appreciated that the present inventions are applicable to a wide variety of infusion pumps and medicaments. By way of example, but not limitation, many of the present inventions are also applicable to infusion pumps that are not cartridge-based (e.g., pumps with refillable reservoirs and single use pumps). Also, the inventions may employ, for fluid displacement, a cartridge with a plunger, a fluid displacement device in the form of a plunger pusher, and a drive mechanism that includes a motor, or other fluid displacement devices, regardless of the type of cartridge or reservoir employed, piston pumps (e.g., electromagnet pumps), MEMS pumps, peristaltic pumps and any other suitable pumps as well as corresponding drive mechanisms. Exemplary infusion pumps that include a cartridge with a plunger, a fluid displacement device in the form of a plunger pusher, and a drive mechanism are described in U.S. patent application Ser. No. 12/890,207, filed Sep. 24, 2010, which is hereby incorporated by reference in its entirety. The present inventions are also applicable to medicaments such as, for example, drugs to mask pain, chemotherapy and other cancer related drugs, antibiotics, hormones, GLP-1, Glucagon, various other drugs that include large molecules and proteins that may require a high level of delivery accuracy, as well as to relatively high concentration insulin (i.e., U-200 and above) such as U-500 insulin.

As noted above, some ambulatory infusion pumps are intended to be worn on a belt, carried in a pocket, or otherwise supported within a holder of some kind (referred to collectively as "pocket pumps"). Such infusion pumps transfer fluid from a reservoir to an infusion set by way of an elongate tube. Subcutaneous access may be obtained by way of a cannula in the infusion set. Other ambulatory infusion pumps are intended to be adhered to the skin at the delivery site (sometimes referred to as "patch pumps"). Here, the cannula or other subcutaneous access device may extend directly from the infusion device. Given these modes of use, patients typically prefer the pump to be as small as possible so that the pump will be more comfortable, less obtrusive, and less visible. In addition, patients want a device that is easy and convenient to use.

Figure 1:
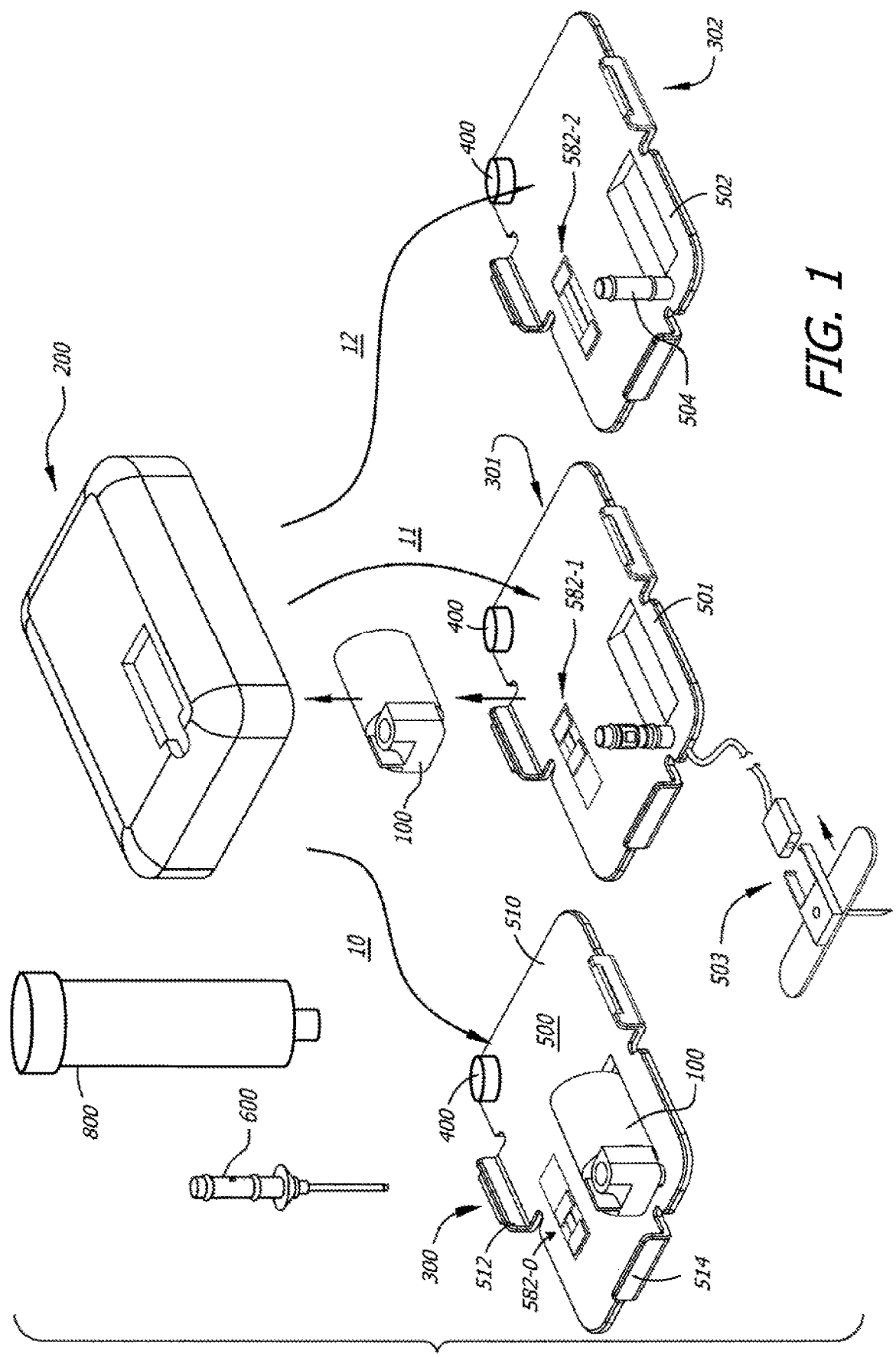
FIG. 1 is an exploded perspective view of an exemplary infusion pump kit including an infusion pump assembly and three baseplate assemblies.

Exemplary ambulatory infusion systems, which are generally represented by reference numerals 10, 11 and 12 in FIG. 1, include a medicament cartridge (or "cartridge") 100, an ambulatory infusion pump assembly (or "pump assembly") 200, and one of the baseplate assemblies 300, 301 and 302. The baseplate assemblies 300, 301 and 302 each include an energy supply 400 and a respective baseplate 500, 501 and 502. The baseplates 500, 501 and 502 are configured to be attached to the pump assembly 200 and, to that end, each includes a plate member 510, a pair of opposing connectors 512, and a hook 514.

Figure 2B:
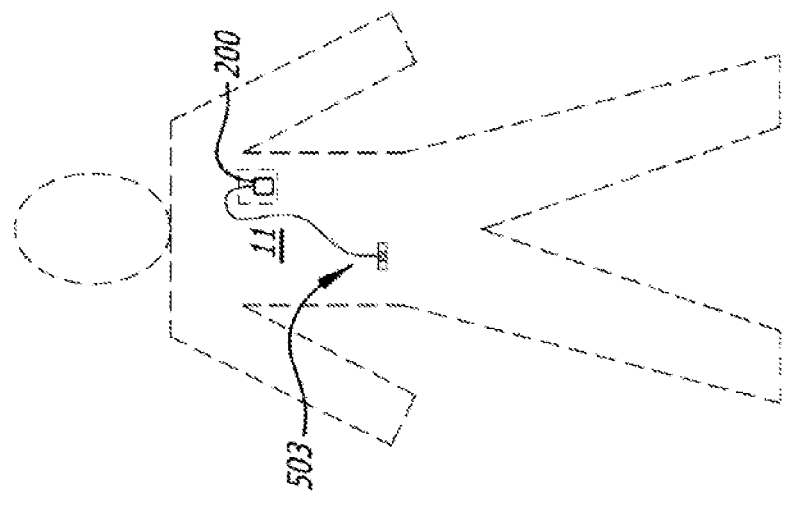
FIG. 2B is a schematic view showing use of an exemplary infusion pump system.
Figure 2A:
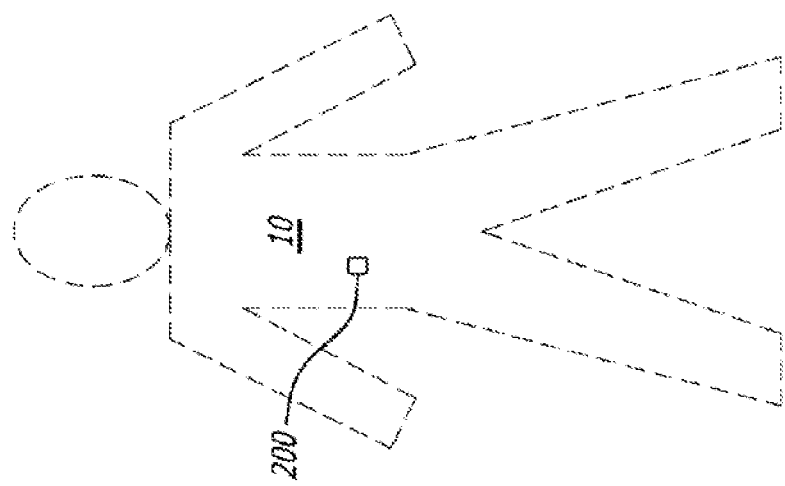
FIG. 2A is a schematic view showing use of an exemplary infusion pump system.

The baseplates 500, 501 and 502 are also configured for different modes of system operation. Baseplate 500 is a body adherable baseplate that may be used in conjunction with a cannula 600 that is directly connected to the cartridge 100 so that the system 10 may be deployed as a "patch-pump" by securing the baseplate to the patient's skin (FIG. 2A). Baseplate 501 is configured to connect the cartridge 100 to an infusion set 503 so that the system 11 may be deployed as a "pocket pump," a "belt-worn pump" or some other wearable pump (FIG. 2B). Baseplate 502 is a medicament non-delivery baseplate that may be used to seal the cartridge 100 during periods of non-use (e.g., by way of plug 504), thereby defining a non-use system 12. In other words, using the same pump assembly (e.g., pump assembly 200), the user may configure the system for use as "pocket pump" or a "patch pump" by simply selecting the appropriate baseplate assembly and attaching the baseplate assembly to the pump assembly. The user may also switch from one configuration to another, by simply removing one baseplate assembly and replacing it with another baseplate assembly. The baseplate assemblies may also be configured for different medicaments, such as different medicament concentrations, and/or different medicament amounts.

In some instances, the cartridge 100 may be detached from a baseplate assembly and inserted into the pump assembly 200 prior to the baseplate assembly being secured to the pump assembly. In other instances, the cartridge 100 may be secured to, integral with or otherwise a part of a baseplate assembly so that the cartridge will be inserted into the pump assembly 200 as the baseplate assembly is secured to the pump assembly. For example, the baseplate assembly 300 includes a cartridge 100 that is secured to the baseplate 500 (e.g., with adhesive) in exemplary system 10, while the cartridge 100 and baseplate assembly 301 are separate structures in exemplary system 11. Baseplate 502 is employed in those instances where the cartridge and baseplate are detached from one another.

It should also be noted here that, in addition to the baseplate, cartridge, and energy supply, some baseplate assemblies may also include the cannula 600 as well as an inserter 800 for inserting the cannula. Other baseplate assemblies with various combinations of these components (e.g. a baseplate and a cartridge that is either secured to the baseplate or separated therefrom) may also be provided. The baseplate assembly components may be integrated together into a single package that can be delivered to the user, as shown, for instance, as baseplate assembly 300' in FIG. 17. In other implementations, some or all of the baseplate assembly components may be provided to the user separately, as user-replaceable parts.

Whether configured as a "pocket pump" or a "patch pump," the system may be configured to provide basal delivery of medicament in accordance with a delivery profile provided by a physician by way of a clinician's programming unit. For example, the system may include a program that stores a number of delivery profiles (e.g., delivery profiles associated with a 24-hour delivery cycle, delivery profiles for particular situations such as sleep or illness, and the like). Each delivery profile specifies multiple doses (or pump "operations") over time, e.g., a particular number of doses at particular times or a particular number of doses per unit time. In some implementations, a dose may be the volume associated with the minimum controllable displacement of a cartridge plunger. The system may also be configured to provide bolus delivery in response to an instruction from a patient remote control. A bolus instruction may come in response to a high glucose level measurement in the case of a diabetic patient, an increase in pain level in the case of a pain management patient, or some other symptom. The system may also be configured to perform other functions, such as ending medicament delivery, in response to instructions from a patient remote control.

The present infusion pumps may be used in conjunction with a wide variety of remote controls. Such remote controls may be used to, for example, allow the user to transmit instructions to the pump assembly or facilitate communication between the pump assembly and the user (e.g., an alarm condition message or other message concerning the conditions of the pump assembly). An exemplary remote control 1000 (FIG. 14) may be configured to facilitate one, some or all of the following operations: (1) turning the remote control 1000 on or off, (2) associating (or "assigning") the remote control 1000 to the pump assembly 200, (3) obtaining status information such as medicament level, battery charge level, and/or alarm conditions, (4) silencing the pump assembly alarm, (5) selecting options that may be associated with the pump assembly alarm such as type of alarm (audible, palpable, and/or visible) and strength/volume of alarm, (6) connecting the remote control to a computer to, for example, update remote control or pump assembly firmware, load and delete delivery profiles stored in the pump assembly or remote control, and otherwise reprogram the pump assembly or remote control, (7) selecting medicament options such as medicament concentrations, (8) selecting and initiating a stored medicament delivery profile, (9) increasing and decreasing medicament dose rate, (10) retracting the plunger pusher from the cartridge to the home position, and/or (11) pausing a dispensing operation. A user may pause delivery in order to remove or replace a patient applied structure (e.g., a baseplate assembly), adjust for a current or anticipated change body condition (e.g., low glucose, vigorous exercise), follow a physician's suggestion, or disconnect the pump assembly from the body for any other reason.

The exemplary remote control 1000 may be configured to generate an indicator, based on information from a controller for pump assembly 200, that is indicative of the amount of time remaining in the current dispensing program and/or the amount of time until the next baseplate assembly replacement and/or the amount of time until the pump assembly battery requires recharging. The indicator may be audible, visible, palpable or combinations thereof. A time remaining indicator may be useful for a variety of reasons. For example, knowledge of the time remaining prior to next baseplate assembly replacement allows the patient to determine, based at least in part on the current time of day and upcoming events (e.g., travel or sleep), whether or not it would be more convenient to replace the baseplate assembly at a time prior to the end of the dispensing program.

The system may also be provided with baseplate assemblies configured for different concentrations of medicament, such as different types of insulin. For instance, U-100 insulin is a relatively low concentration insulin containing 100 international units (IU) of insulin activity per 1 ml and, accordingly, a 2 ml cartridge reservoir stores 200 IUs. One common insulin dose is 0.5 IU, which equates to a dispensed volume of 5 microliters (µl) of U-100 per dose, 400 doses per 2 ml reservoir, and about 4.5 days of therapy at the common dosage. However, higher concentration insulins are commercially available. Humulin® R U-500 insulin, which is available from Eli Lilly and Company in Indianapolis, Ind., contains 500 IU/ml. Additionally or alternative, different baseplate assemblies may be configured for different medicament fill volumes, to correspond to the amount of medicament used in the baseplate assembly lifetime. Therefore, a variety of baseplate assemblies can be provided containing different concentrations and/or amounts of medicament, such as various concentrations and/or units of insulin. In addition to baseplate assembly packaging and labeling, the different baseplate assemblies may include visual cues to differentiate the various baseplate assemblies. For instance, baseplate assemblies with different concentrations of medicament or different medicament fill volumes may use different colors for the cartridge and/or baseplate of the baseplate assembly.

When a baseplate assembly is attached to the pump assembly, the pump assembly may automatically detect the version of baseplate assembly that was attached, as described further below. Alternatively, the patient or a clinician may program the pump, such as via a remote control, to indicate the type of baseplate assembly attached. In a manner such as this, a patient can access a variety of medicaments for use with a single pump assembly.

As such, parts of the present systems may be considered the reusable parts, while other parts may be considered the disposable parts. In the illustrated embodiments, the pump assembly 200, which includes structures such as the motor and various mechanical structures, the pump assembly controller, and a rechargeable battery, is reusable, while the baseplate assembly, which may include some or all of a baseplate (such as one of the baseplates 500-502), a cartridge 100, an energy supply 400, a cannula 600, and a cannula inserter 800, is disposable. Another disposable baseplate assembly 300' is shown in FIG. 17.

The exemplary system is, as noted above, a cartridge-based system in that medicament cartridges 100 (which may or may not be included as part of baseplate assembly 300 or 301) are inserted into the pump assembly 200 and later removed from the pump assembly. The cartridges 100 may also be, but are not required to be, prefilled and disposable. Prefilled cartridges are advantageous for a variety of reasons. By way of example, but not limitation, some users prefer to avoid cartridge filling procedures because they are inconvenient and tend to involve needles. User-based refilling also increases the likelihood that air bubbles will be introduced into the cartridge, while prefilling by the manufacturer of the cartridge and/or the medicament can be accomplished without any substantial introduction of air bubbles using, for example, a vacuum filling procedure.

Referring to FIG. 10, the exemplary medicament cartridge 100 may include a barrel 102 that defines a medicament reservoir 104, a plunger 106, and a manifold 108. The manifold 108, which may include a through-bore 116, may be used to connect the reservoir to, for example, cannulas and baseplate structures. The plunger 106 moves within the cartridge to vary the volume of medicament within the reservoir. The cartridge 100 may also be provided with a plug 110 that prevents leakage from a prefilled reservoir (e.g., prefilled in a vacuum with U-500 insulin) during packaging, shipping, storage and handling, and can be manually removed by the user.

At least some of the exemplary implementations may employ pressure data in various contexts. For example, a pressure sensor may be used to detect occlusions that are impeding, or completely preventing, medicament flow. To that end, a medicament cartridge may include some or all of the pressure sensor itself. The pressure sensor may also be used to detect the presence of a cartridge in the pump assembly, as is also described below.

Figure 3:
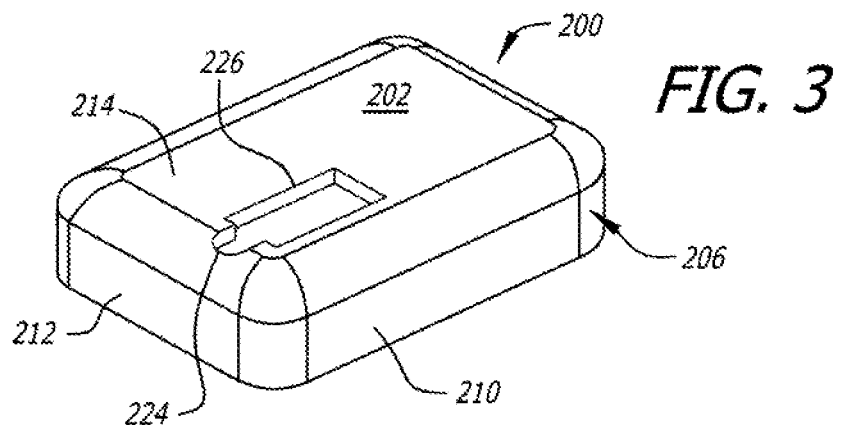
FIG. 3 is a perspective view of an exemplary pump assembly.

Briefly, the exemplary pump assembly 200 may include an external housing ("housing"), which is generally represented by reference numeral 202 in FIG. 3, and a pump module that is located within the housing, and is therefore not shown. Other structures that may be carried within the housing 202 include, but are not limited to a rechargeable battery, a pump assembly controller and associated circuitry 237 (FIG. 6), and an alarm. When the baseplate assembly is attached to the pump assembly and medicament cartridge 100 is in operational position within the pump assembly 200, the cartridge plunger 106 will be proximate to and facing a plunger pusher 250 of the pump module (see FIG. 10). A drive mechanism of the pump module may then drive the plunger pusher relative to the cartridge plunger to controllably and precisely dispense medicament from the cartridge reservoir.

As noted above, the exemplary pump assembly 200 may include an alarm that is carried within the housing 202. The alarm may be audible (e.g., a buzzer), palpable (e.g., a vibrator), visible (e.g., an LED with a portion that extends through the housing 202) and/or any combination thereof. A number of conditions may result in alarm activation in the exemplary embodiments. For example, alarm conditions include, but are not limited to, low or dead battery, occlusion, low or empty reservoir, hardware self-test, firmware error, absence of a baseplate, device fall-off, baseplate/pump assembly disconnection, battery charge over-temperature, telemetry fault, motor error, unable to find plunger, and/or charging faults.

Figure 4:
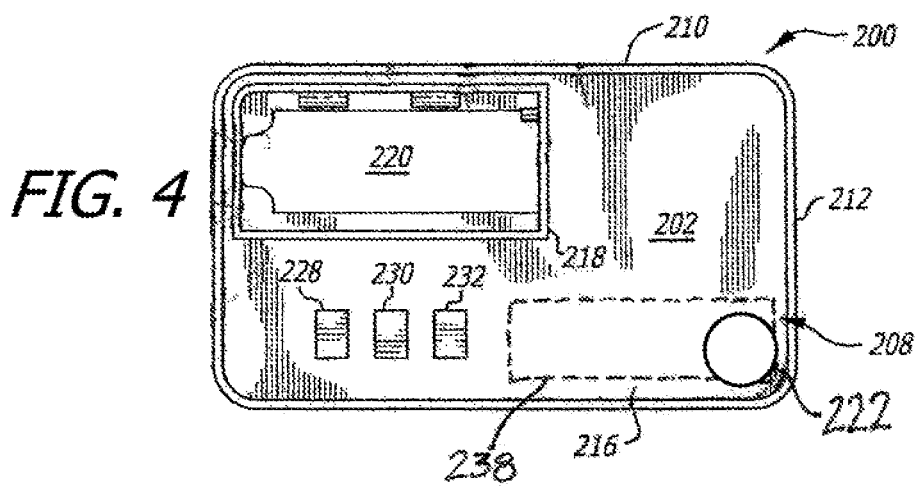
FIG. 4 is a bottom view of the exemplary pump assembly illustrated in FIG. 3.

Referring to FIGS. 3-4, the housing 202 has a top portion 206 and a bottom portion 208. The top portion 206, which includes two side walls 210, two end walls 212, a top wall 214 and rounded corners therebetween, generally defines the internal volume in which the pump module and other pump assembly components are carried, as well as the overall volume of the pump assembly 200. The bottom portion 208 includes a bottom wall 216, which functions as a cover for most of the internal volume. The outer surface of the top wall 214 defines the "top face" or "top surface" of the housing 202, and the outer surface of the bottom wall 216 defines the "bottom face" or "bottom surface" of the housing.

There is a cartridge insertion opening 218 in the bottom wall 216 through which the cartridge 100 is inserted into the cartridge receiving area 220 when baseplate assembly 300 is attached to pump assembly 200. Bottom wall 216 also includes a baseplate energy supply receiving area (or "recess") 222 into which the energy supply 400 projects when a baseplate assembly (e.g., baseplate assembly 300) is attached to pump assembly 200. This arrangement facilitates the transfer of energy from the baseplate energy supply 400 to the rechargeable battery 238, as described below.

The top wall 214 of the housing 202 may be provided with one or more openings. For example, an inserter opening 224 may be provided in the housing top wall 214 to enable access for an inserter 800 or 800'. Such access may be required for a cannula insertion process, such as that described below with reference to FIGS. 10-13.

Figure 5:
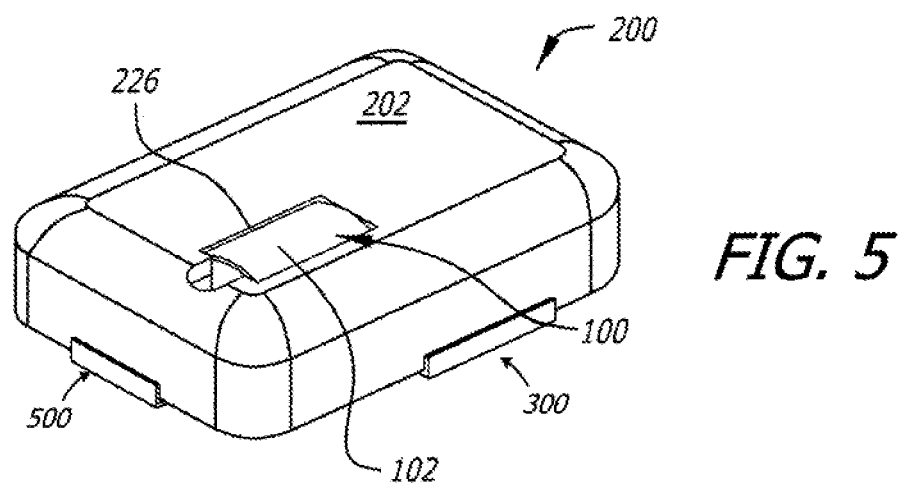
FIG. 5 is perspective view of the exemplary pump assembly illustrated in FIG. 3 with a baseplate attached and associated cartridge inserted.

The top wall 214 of the housing 202 may also be provided with a cartridge opening 226 for the top of cartridge 100. The inserter opening 224 and cartridge opening 226 are merged into a single opening in the illustrated embodiment. Such openings may be separate in other embodiments. Cartridge opening 226 facilitates observation of the medicament and plunger within a cartridge formed from transparent material. Additionally, in the illustrated embodiment, the pump assembly 200 is configured (i.e., sized, shaped, etc.) such that a portion of the associated cartridge (e.g., cartridge 100) may protrude through the cartridge opening 226 when the baseplate assembly is in place and the cartridge is in the cartridge receiving area 220. For example, the relative configurations of the baseplate assembly 300, cartridge 100 and pump assembly 200 may be such that the cartridge body protrudes slightly (e.g., about 0.40-1.00 mm, or five percent of the reservoir volume) through the opening 226 in the housing top wall 214, as is illustrated in FIG. 5. The bulk of the cartridge body will, however, be located below the inner surface of the top wall 214. The length of the cartridge opening 226 is substantially equal to the length of the cartridge reservoir, with appropriate clearance, while the width is somewhat less than the diameter of the cartridge. For example, the width of the opening 226 may be about 60 to 90% of the diameter and is about 83% in the illustrated implementation. In other implementations, the cartridge opening 226 may be eliminated and replaced by a protrusion that covers the cartridge and is part of the housing top wall 216.

A plurality of electrical contacts 228, 230 and 232 may extend through (or be carried on) the housing bottom portion 208, as is illustrated in FIG. 4. As discussed in greater detail below, two of the contacts (e.g., contacts 228 and 230) may be used to electrically connect the pump assembly 200 to a battery recharger (e.g., charger 700 in FIG. 6) and all of the contacts, at least in some implementations, may be used by the pump assembly during a baseplate identification procedure described below.

With respect to dimensions, some embodiments of the exemplary housing 202 may have the following dimensions: length dimensions of 42 mm+/−1.0, 42 mm+/−0.10, 40+/−0.10 mm or 40+/−5.0 mm; width dimensions of 34 mm+/−1.0, 34 mm+/−0.10 mm, 32 mm+/−1.0 mm, 32 mm+/−0.10 mm or 32 mm+/−5 mm; overall thickness or height dimensions of 9 mm+/−1.0 mm or 9 mm+/−0.10 mm; and wall thickness dimensions on the order of 1.0 mm+/−0.10 mm. Suitable housing materials include, but are not limited to, plastic or other materials having a modulus of elasticity of 0.2-1.0 million psi.

As mentioned above, pressure sensors may be provided to, among other things, detect occlusions in a cannula or infusion set tube. Occlusions may occur for any number of reasons including, but not limited to, cannula kinks caused by movement of the pump assembly relative to a deployed cannula, kinks in the infusion set tube, or granuloma formation at the outlet end of a cannula. The structures that are used to sense pressure may also be used to, for example, sense baseplate assembly attachment, medicament cartridge presence, and/or alignment within a pump assembly. In at least some implementations, one portion of the pressure sensor may be part of the medicament cartridge and another portion of the pressure sensor may be part of the pump assembly. Other exemplary detectable structure arrangements include, but are not limited to, a magnetically permeable structure carried on a diaphragm and movable relative to a coil; and an optical element carried on a diaphragm and movable relative to an optical sensor; and an electrical conductor carried on a diaphragm and movable relative to a pair of switch contacts. It should also be noted that, with respect to the implementations that include a pressure sensor, the present inventions are not limited to pressure sensor arrangements that include a diaphragm, or to pressure sensor arrangements that include a cartridge portion and a pump assembly portion. For example, a medicament cartridge may include a pressure sensor that communicates with the pump assembly by way of electrical contacts.

The battery that drives the motor may be a rechargeable battery, such as a rechargeable lithium polymer battery or a rechargeable lithium ion battery. At least some implementations will employ a rechargeable battery having a fully charged, open circuit voltage of generally about 3.7 Volts, or between about 3.0-4.24 Volts. One advantage of lithium polymer and lithium ion batteries is that they can be recharged quickly, have high energy density, and have desirable linear decay that facilitates accurate charge state indication.

Figure 8:
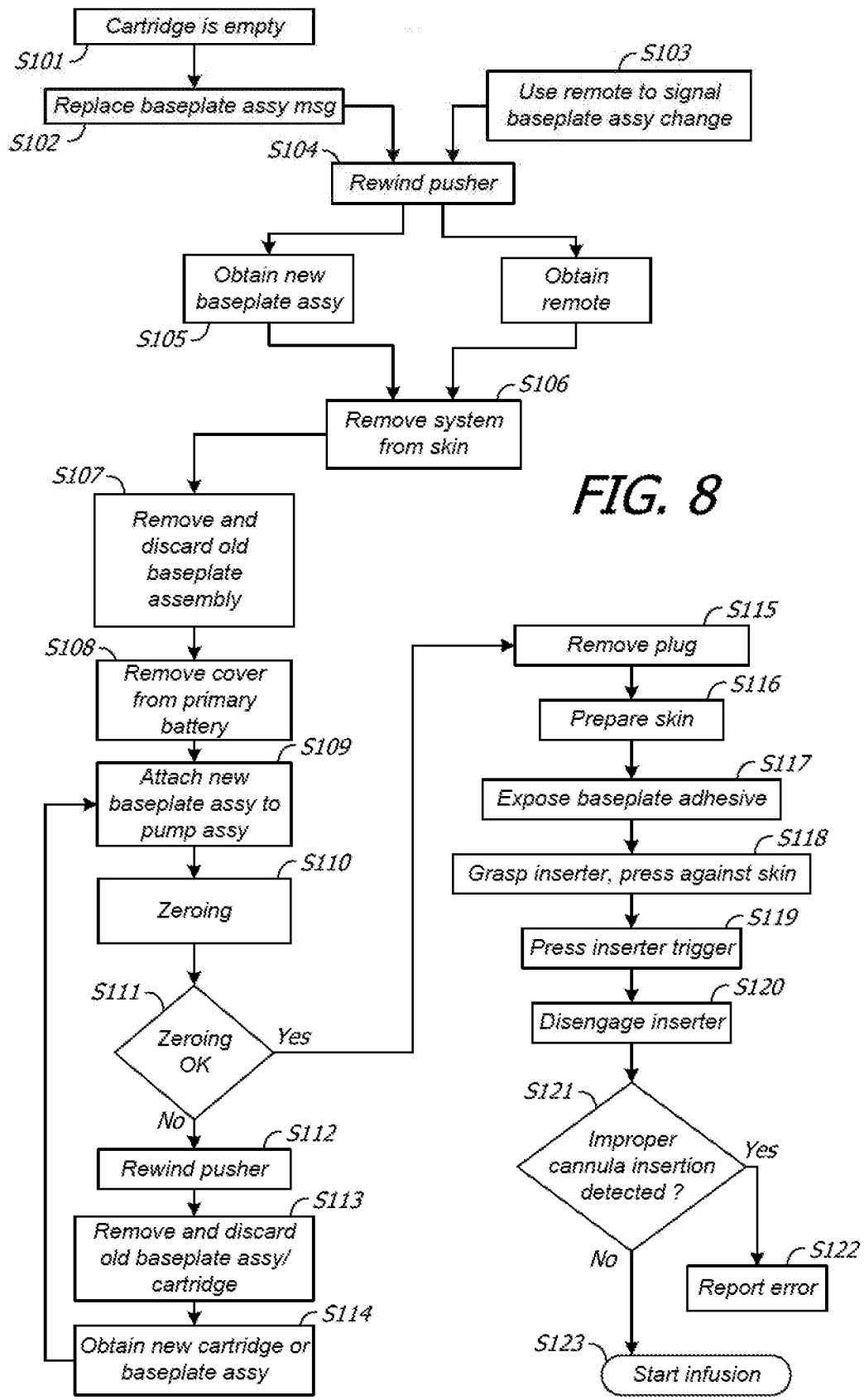
FIG. 8 is a flow chart showing an exemplary baseplate assembly removal and replacement method.

Turning to FIG. 8, the exemplary rechargeable battery 238 may be carried within the pump assembly housing 202. Additionally, because the battery 238 is rechargeable, e.g., via external recharging contacts 228 and 230 or the baseplate energy supply 400, the exemplary housing 202 does not include a door or a cover to provided access to the battery, and the exemplary housing may be sealed (i.e., it cannot be opened without damage thereto).

Figure 6:
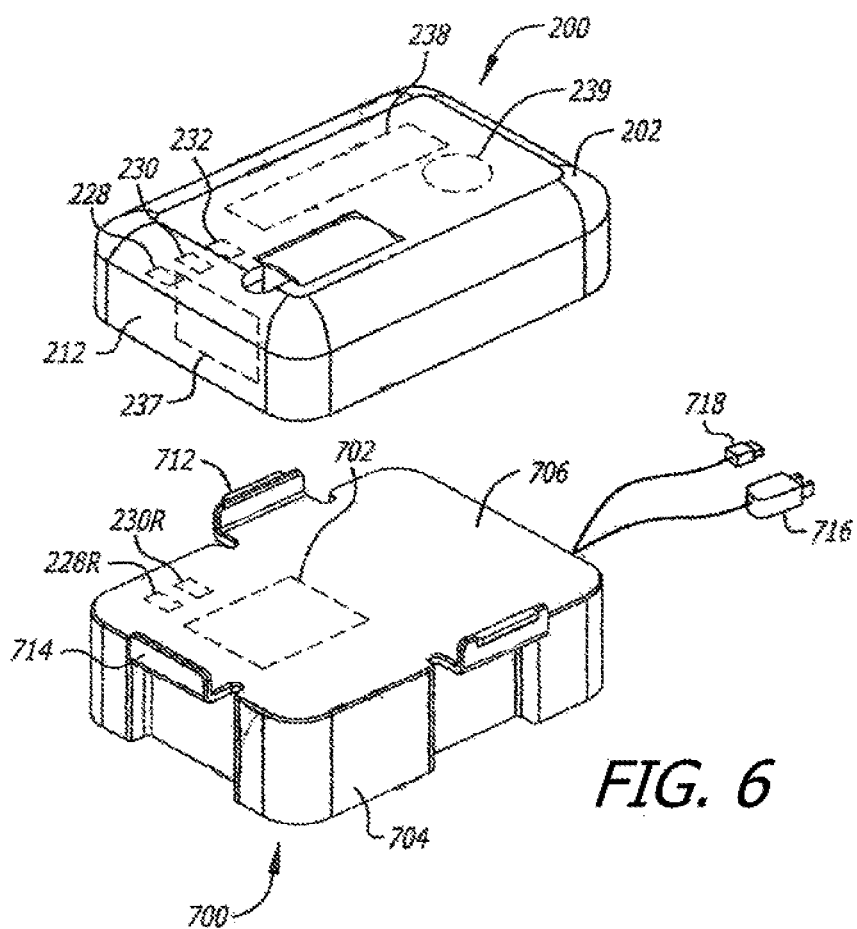
FIG. 6 is a perspective view of an infusion pump assembly being attached to a battery recharging device.

One example of a battery recharger, which is generally represented by reference numeral 700 in FIG. 6, includes recharging circuitry 702 (e.g., a controller and power circuitry) within a housing 704. The top portion of the recharger housing 704 may include a plate 706, a pair of opposing connectors 712, a hook 714, and electrical contacts 228R and 230R. Power and data connectors 716 and 718 may also be provided. The respective configurations of the pump assembly 200 and battery recharger 700 are such that, when the pump assembly is placed on the plate 706 with an end wall 212 abutting the hook 714, the pump assembly recharge contacts 228 and 230 will be electrically connected to the recharger contacts 228R and 230R.

It should be noted here that the present pump assemblies and battery rechargers are not limited to those which make a direct electrical connection through the use of electrical contacts. By way of example, but not limitation, inductive coupling may be employed.

Figure 15:
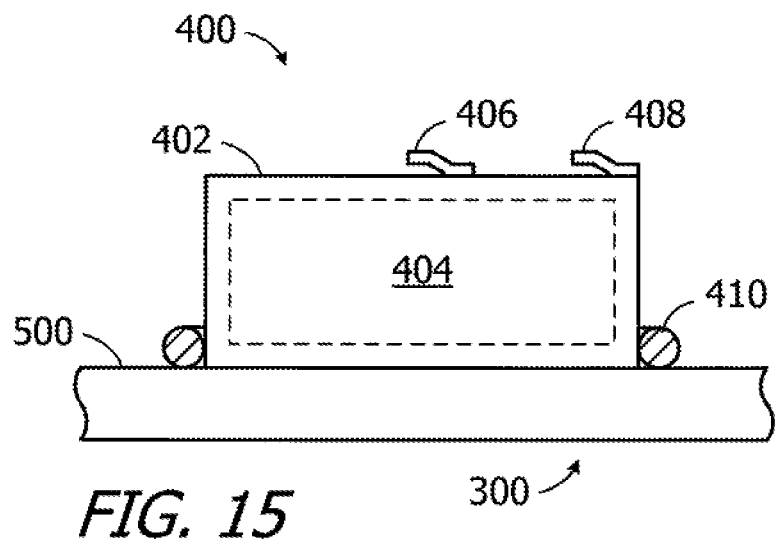
FIG. 15 is a side view of a portion of one of the baseplate assemblies illustrated in FIG. 1.
Figure 16:
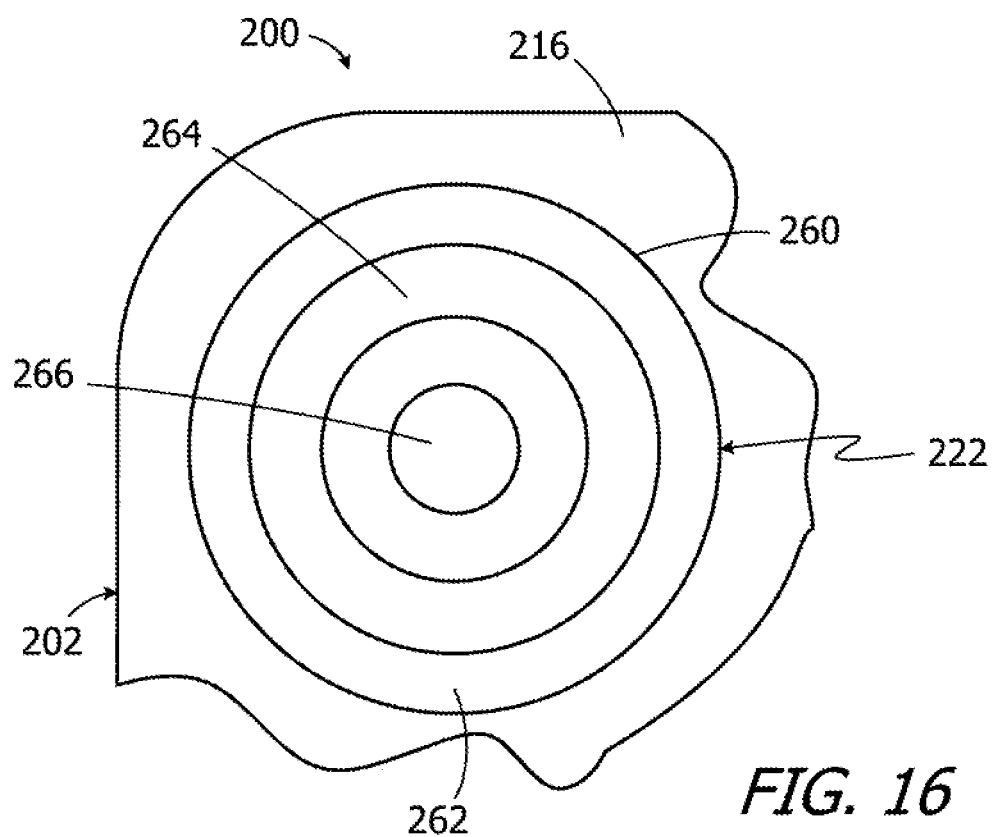
FIG. 16 is a bottom view of a portion of the pump assembly illustrated in FIG. 1.

In addition or as an alternative to the above, rechargeable battery 238 may be recharged by the baseplate energy supply 400 carried on baseplate 500-502 (see FIG. 1). Referring to FIG. 15, the exemplary energy supply 400 includes a housing 402 and an energy storage device 404 within the housing. Any suitable energy storage device may be employed. Exemplary energy storage devices include, but are not limited to, primary cell batteries, fuel cells and capacitive storage devices. Exemplary primary cells include alkaline batteries and Zinc-air batteries, including those in the form of small button cells of the type commonly used in hearing aids. Such batteries are sometimes referred to as "disposable" batteries. The energy supply also includes a pair of flexible electrical contacts 406 and 408 that are respectively connected to the anode and cathode of the energy storage device 404. A seal 410, such as an a-ring seal, extends around the base of the energy supply housing 402.

As noted above, the baseplate energy supply 400 projects into the baseplate energy supply receiving area 222 when a baseplate assembly (e.g., baseplate assembly 300) is attached to the pump assembly 200. To that end, the receiving area 222 is defined by a side wall 260 and an end wall 262 that are formed in the bottom wall 216 of the housing 202. A pair of electrical contacts, such as the illustrated annular contact 264 and circular contact 266, are located on the end wall 262. The contacts 264 and 266 are connected to the circuitry 237. The respective configurations of the receiving area 222 and the baseplate energy supply 400 are such that the energy supply contacts 408 and 408 will engage the receiving area contacts 264 and 266, and the seal 410 will engage the side wall 260 to prevent moisture ingress, when the baseplate assembly 300 is connected to the pump assembly 200.

It should also be noted here that the present inventions are not limited to the exemplary receiving area 222 and baseplate energy supply 400 described above. For example, the baseplate energy supply 400 may be provided with other types of flexible or otherwise outwardly biased electrical contacts. Alternatively, or in addition, the receiving area 222 may be provided with flexible or otherwise outwardly biased electrical contacts. One or both sets of electrical contacts may also be eliminated. For example, in those instances where the baseplate energy storage device is a button battery, the baseplate energy supply and the infusion pump energy supply receiving area may be configured such that contacts within the receiving area directly contact the anode and cathode cans of the battery. Inductive coupling may be employed in other implementations.

At least some implementations will employ an energy storage device 404 having a fully charged, open circuit voltage of generally about 1 Volt, or between about 1.0-1.5 Volts.

The energy storage device 404 may be a Zinc-air battery, the advantages of which include high energy density, small size and wide availability. Zinc-air batteries obtain their energy from the electro-chemical reaction of oxidizing zinc with oxygen from the air. Therefore, the housing 402 may be provided with an aperture and a cover that can be used to prevent air from initiating the reaction and activating the battery. As such, in some embodiments, prior to use, a cover must be removed from the housing 402. Other primary batteries (e.g., an alkaline battery) that may be used to recharge rechargeable battery 238 may not require removal of a battery cover.

Returning to the above example, the recharging of rechargeable battery 238 with baseplate energy supply 400 may use a DC-to-DC converter, for instance, within circuitry 237 (FIG. 6). The DC-to-DC converter may be used to convert the nominal 1 V from the energy storage device 404 to a voltage that is greater than the voltage of the battery 238, e.g., greater than a nominal 3.7 V, to recharge the rechargeable battery 238. In some implementations, the recharging process may be controlled by the pump assembly controller, such as by circuitry 237 associated with the pump assembly controller, or by other circuitry (such as dedicated circuitry or a DC-to-DC converter semiconductor chip), or some combination thereof. In such implementations, the pump assembly controller (or processor circuitry, etc.) may monitor the primary battery voltage and actively control the recharging process, such as when to commence or cease charging. In other embodiments, the recharge process and/or primary battery voltage may not be controlled or monitored, and the recharging proceeds until the primary battery is exhausted.

Given the relatively close proximity of the rechargeable battery 238 to the medicament cartridge 100, heat from the battery 238 could possibly increase the temperature of the medicament during recharging, especially during rapid recharging. The medicament temperature may be relevant to certain medicaments such as insulin, for example, which can be damaged and have its viability become undefined at about 37° C. Accordingly, a temperature sensor 239 (e.g., a thermistor or thermocouple) may also be carried within the pump assembly housing 202 in such a manner that the temperature sensor can sense the temperature of the medicament in the cartridge 100 (or a temperature that is at least representative thereof). For example, the temperature sensor 239 may be carried on the circuit board associated with the exemplary pump assembly controller. Temperature sensing apparatus, such as a heat pipe that extends to the reservoir (not shown), may also be included on some cartridge implementations. The temperature information may be provided to the pump assembly controller, or to other circuitry such as in recharger 700, or another controller (collectively referred to as the "recharge controller"), to modulate the battery recharging process as a function of temperature sensed by temperature sensor 239.

Figure 7:
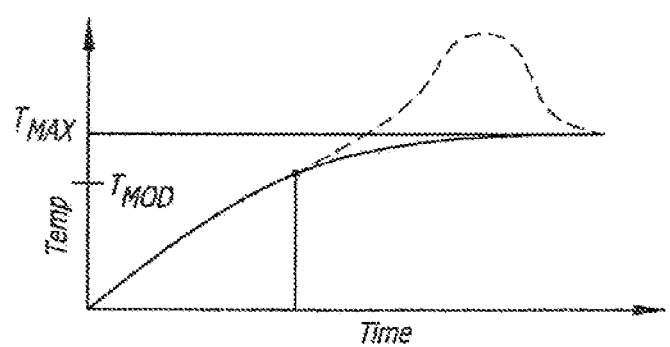
FIG. 7 is a graph showing recharging temperature during a exemplary battery recharging method.

Modulation of the recharging process may be accomplished by, for example, selectively increasing or decreasing the rate at which the battery 238 is recharged (e.g., by controlling current) as a function of sensed temperature. For example, and referring to FIG. 7, the modulation process may be designed to perform temperature control in a manner that prevents the sensed temperature from overshooting the predetermined maximum temperature ($T_{MAX}$) as shown by the dashed lines. To that end, as temperature reaches a modulation temperature ($T_{MOD}$) below the maximum temperature $T_{MAX}$, the recharging rate is reduced to keep the temperature at or below the maximum temperature $T_{MAX}$.

It should also be noted that it may be difficult for the battery 238 to provide enough current if the temperature within the pump housing 202 is low. The temperature sensor 239 may, therefore, be used to monitor temperature during operation of the pump assembly 200. An alarm may be actuated by the recharge controller if the temperature is too low.

In at least some implementations, the recharge controller may be configured to identify and/or prevent charging faults, such as battery overcharge that can cause the battery to swell, vent and otherwise stress other components within the pump assembly.

With respect to the amount of time until the rechargeable battery 238 requires recharging, the pump assembly may be provided with a battery management chip (or other suitable battery management apparatus) that determines when recharging is necessary. For example, recharging may be necessary when the battery voltage is reduced from the fully charged voltage to a predetermined voltage that is less than the fully charged voltage. The amount of time remaining may be estimated by the battery management apparatus based on factors such as battery age, battery temperature, and the dispensing program. The battery management apparatus may be part of, or operably connected to, the pump assembly controller. The controller is configured to generate a signal indicative of the amount of time remaining until the battery will require recharging.

Alternatively, and in particular when using the baseplate energy supply 400 with the baseplate assembly, the rechargeable battery 238 is recharged to full capacity each time a new baseplate assembly is attached to the pump assembly. In other words, when the patient requires or desires a new medicament cartridge, the new baseplate assembly will include the baseplate energy supply 400, which will recharge the rechargeable battery. The rechargeable battery 238, under normal operation (e.g. with no battery failure or discharge problems), will maintain a charge longer than the time it takes to empty cartridge 100. As such, if the system is operating as usual, the patient will not receive a message that rechargeable battery 238 needs to be recharged.

As noted above, and as illustrated for example in FIGS. 1, 2A and 2B, the present infusion systems may include any one of a variety of different baseplate assemblies (shown without cartridge 100 and inserter 800 for ease of differentiation) in combination with a pump assembly (e.g., pump assembly 200). As an example, FIG. 17 illustrates an exemplary baseplate assembly 300' that includes baseplate 500', inserter 800', cartridge 100', and baseplate energy supply 400'. Each baseplate assembly may be configured for a different mode of system operation. For instance, baseplate 500 is a body adherable baseplate that may be used in conjunction with a cannula such as cannula 600 connected to the cartridge 100 so the system may be deployed as a "patch pump." Baseplate 501 is configured to connect the cartridge 100 to an infusion set 503 so that the system may be deployed as a "pocket pump," a "belt-worn pump" or some other wearable pump. Baseplate 502 is a medicament non-delivery baseplate that includes a plug 504 which may be used to seal the cartridge 100 during periods of non-use.

As also described above, the system may be provided with baseplate assemblies configured for different types or concentrations of medicament, such as different insulin concentrations. Additionally or alternatively, a variety of baseplate assemblies may be provided with different medicament fill volumes, to correspond to the amount of medicament used during the baseplate assembly lifetime. Therefore, an assortment of baseplate assemblies is possible, containing different types, concentrations and/or amounts of medicament, such as various concentrations and/or units of insulin. These different baseplate assemblies may be distinguished by packaging, labeling, or other cues such as different colors for the cartridges and/or baseplates of the various baseplate assemblies.

Additionally, and as discussed below, pump assembly 200 and baseplate assemblies 300-302 may be respectively configured such that a pump assembly can determine which one of a variety of baseplate assemblies is attached to the pump assembly and then prepare to proceed in accordance with the operational mode associated with that baseplate assembly. Also, although the exemplary baseplate assemblies are described herein in the context of the exemplary cartridge 100 and the exemplary pump assembly 200, the present baseplates and baseplate assemblies may be used in conjunction with other cartridges, cartridge-based pumps, and pumps that are not cartridge-based.

Exemplary baseplates for use with the baseplate assemblies of the present inventions, exemplary cannula designs, fluidic connection between a medicament cartridge and the cannula, cooperation between the cannula and baseplate assemblies, for instance, to prevent axial movement of the cannula relative to the baseplate and patient, attachment of an infusion set to the cartridge of the baseplate assembly, configurations and uses of a non-delivery baseplate, arrangements and structures for attaching baseplate and pump assemblies, skin adhesive designs, occlusion sensors, and various inserters may be as described in U.S. patent application Ser. No. 12/890,207, filed Sep. 24, 2010.

The dimensions of the baseplate assembly may correspond to those of the associated pump assembly. In the context of the exemplary pump assembly 200 described above, the plate member may be 1 mm thick, with length/width relationships such as 42 mm×34 mm, 40 mm×32 mm, and/or 39.0-43.0 mm×31.0-35.0 mm.

It should also be noted that the present inventions include kits which contain various combinations of baseplates, at least two of the baseplates being different. Additionally or alternatively, kits or other packages may include various baseplate assembly components, such as medicament cartridges and/or cannula inserter, as user replacements. Kits may also include a pump assembly. The baseplate assemblies in such kits may also include the detection instrumentalities discussed below. The components of the present kits (e.g., combination of various baseplate assemblies and/or components) may be stored in a common package, with individual packages for each component if necessary, and provided to the user in the common package. Other components that may be provided in such kits include, but are not limited to, inserters that are preloaded with a cannula and cleaning swabs. A recharger may also be provided in a kit that includes a pump assembly.

It should be noted here that, but for the issue of priming, the dispensing procedures associated with an infusion system "patch pump" configuration, which may include a pump assembly 200 and a baseplate assembly 300 are substantially the same as the dispensing procedures associated with a "pocket pump" configuration, which may include a pump assembly 200 and a baseplate assembly 301 (see FIG. 1). With a "patch pump" configuration, priming is not necessary because the volume of the associated cannula will be very small and there is a direct connection between the cannula and the medicament cartridge. Priming is, however, required to fill the infusion set tube (FIG. 1) in a "pocket pump" configuration prior to the onset of medicament delivery. For instance, 20-30 µl may be required to fill the entire infusion set tube and, accordingly, the priming procedure may involve the rapid delivery of 10-15 IUs of U-500 insulin to the tube. The present inventors have determined that it would be advantageous to prevent users from initiating a priming procedure when the system is in the "patch pump" configuration, with a cannula positioned to deliver medicament essentially directly from the medicament cartridge to the patient, because rapidly delivering 10-15 IUs of insulin to the patient could adversely affect patient health.

To prevent such undesirable outcomes, and for user convenience in other situations involving the choice between a variety of baseplate assemblies, at least some of the present baseplate assemblies may be provided with a baseplate identification device and at least some of the present pump assemblies may be provided with structure that cooperate with a baseplate identification device in such a manner that the pump assembly controller can make a "baseplate type" determination. For example, the baseplate identification devices may be carried by the baseplates and may be detectable by the pump assembly as well as distinguishable from one another. Once the "baseplate type" determination is made (e.g., baseplate assembly 300 versus baseplate assembly 301), the pump assembly will proceed in a manner, or mode of operation, that is appropriate for the attached baseplate assembly. For example, if baseplate assembly 300 is detected, the pump assembly controller will not including priming as part of the delivery process and, in some implementations, will prevent the user from manually implementing a priming procedure. If, on the other hand, baseplate assembly 301 is detected, then the delivery process may include appropriate priming of the infusion set tube.

In other embodiments, the identification process may additionally or alternatively distinguish between baseplate assemblies with cartridges containing different medicaments, different concentrations of a medicament, and/or varying amount of medicaments. For instance, if the pump assembly determines that the baseplate assembly is carrying a high concentration medicament, such as U-500 insulin, it can appropriately adjust the dispensing program. If, on the other hand the pump assembly senses a baseplate assembly with a lower concentration medicament, such as U-100 or U-200 insulin, it can provide a proper dispensing program for that concentration. As another example, the pump assembly may detect a baseplate assembly with a certain amount of medicament, and make appropriate adjustments to, for instance, display the medicament level and/or warn the patient when the medicament level is low.

A wide variety of baseplate identification instrumentalities and identification methodologies may be employed, and the present inventions are not limited to any particular instrumentalities and methodologies. Various illustrative examples of such instrumentalities and identification methodologies are described in U.S. patent application Ser. No. 12/890,207, filed Sep. 24, 2010. In one such example, baseplate assemblies 300, 301 and 302 may have respective identification devices 582-0, 582-1 and 582-2 (see FIG. 1), each of which includes a pair of electrical or optical contacts or the like that align and electrically or optically couple (or the like) to a respective two of the three electrical or optical contacts 228, 230 and 232 or the like associated with the pump assembly (FIG. 4) when a baseplate assembly is secured to the pump assembly. For instance, the pump assembly controller may cause voltage to be applied across the pump assembly electrical contacts 228, 230 and 232 and may measure resistance (or another suitable variable) between contact pairs 228/230, 230/232 and 228/232. The pump assembly controller may store information which indicates the resistance levels that correspond to particular baseplate assemblies, and use the resistance measurement to identify the attached baseplate assembly. In one of the other examples described in U.S. patent application Ser. No. 12/890,207, a wide range of resistance values are possible by employing a variety of resistors, two contacts on the baseplate assembly, and two contacts on the pump assembly.

At the most basic level, use of the exemplary infusion pump system 10 (or 11, etc.) illustrated in FIG. 1 involves obtaining a new baseplate assembly 300 (or 301, etc.), connecting the baseplate assembly to the pump assembly, peeling the cover from the baseplate adhesive layer, gaining subcutaneous access, and initiating a medicament delivery operation. In some instances, use may involve additional steps such as removing the cover from baseplate energy supply 400 (if a Zinc-air battery is employed) or pulling the pull-before-use-plug 110 from cartridge 100 of the baseplate assembly, if necessary. Various aspects of the basic operation of the present systems are described below. Operation of a system does not necessarily require all of the steps each time the system is deployed, and the order of some of the steps may be changed. Operation is also discussed below, in the exemplary context of the above-described pump assembly 200 and patch pump baseplate assembly 300, through the use of a flow chart (FIG. 8) as well as through illustrations of the exemplary system itself in various states (FIGS. 9-14). The discussion is, however, equally applicable to other patch pump implementations, as well as to pocket pump implementations with minor variations. Also, unless otherwise indicated, the actions and determinations performed by the pump assembly 200 are controlled by the pump assembly controller and further references to the controller are omitted in the interest of brevity.

Referring first to FIG. 8, use of the present systems may involve removal of a baseplate assembly from a pump assembly. This may occur (in some instances automatically) when the medicament cartridge is empty (e.g. when the plunger pusher 250 is at the end of the pusher stroke, as described in more detail in U.S. patent application Ser. No. 12/890,207) (Step S101) and a "replace baseplate assembly" message or alert is presented (Step S102), or when the pump assembly controller receives a user-initiated "replace baseplate assembly" signal from the remote control 1000 (Step S103). The user may desire to replace a baseplate assembly before the medicament cartridge is empty for a variety of reasons such as, for example, to accommodate the user's sleep or travel schedule, when the medicament appears cloudy or otherwise exhibits a loss of effectiveness, when a dispensing problem arises, or due to a prescribed change in medicament. Whether automatic or user-initiated, the plunger pusher 250 will be returned to the fully retracted home position (Step S104). The user may then obtain a new baseplate assembly (such as baseplate assembly 300 shown in FIG. 1, containing cartridge 100, energy supply 400, baseplate 500, cannula 600, and inserter 800, or baseplate assembly 300' shown in FIG. 17, containing cartridge 100', energy supply 400', baseplate 500', cannula 600' (not shown), and inserter 800') and the remote control 1000 (if not already at hand) (Step S105). The pump assembly 200 and baseplate assembly 300 may then be removed from the skin, separated, and the baseplate assembly 300 discarded (Steps S106 and S107).

Next, the cover (if present) may be removed from energy supply 400 (Step S108) and the new baseplate assembly 300 may then be attached to the pump assembly 200 (Step S109). The plug 110 may remain in the cartridge through-bore 116 for a pusher zeroing procedure described in detail in U.S. patent application Ser. No. 12/890,207 (Step S110). The zeroing procedure may be user-initiated or may be an automatic aspect of pump operation. If the results of the zeroing procedure are negative, the pusher is withdrawn from the cartridge, the baseplate assembly 300 or at least medicament cartridge 100 is removed and discarded, a new baseplate assembly or cartridge is inserted, and the zeroing procedure is repeated (Steps S111, S112, S113 and S114). Alternatively, if the results of the zeroing procedure are positive, the pusher is withdrawn and the plug 110 may be removed (FIG. 10) (Step S115).

The user may clean the skin surface S onto which the baseplate 500 of baseplate assembly 300 will be adhered, and liner 544 may be removed to expose a baseplate adhesive layer 542, as illustrated in FIGS. 9 and 10 (Steps S116 and S117). Also shown in FIG. 10 is an exemplary cannula inserter 800, with cannula 600 in its initial position, prior to insertion. The inserter 800 may include a movable member 802 within a housing 804, and a trigger-type actuator 806 that acts on the movable member. The exemplary actuator 806 may have a rotatable or pressable trigger 808 and a compressed spring or other biasing device 810. A trocar 812 is carried on the movable member 802. A cannula 600 is pre-mounted on the trocar 812 such that the sharp distal end of the trocar extends beyond the cannula tube 612. The inserter 800 may also be configured to withdraw the trocar back into the housing 804 after the cannula is deployed.

In other embodiments, the initial position of cannula 600 is at least partly within through-bore 116, such that plug 110 is unnecessary. When cannula 600 is initially positioned within through-bore 116, it provides a seal against the medicament outlet 117 of the cartridge 100. As such, plug 110 may be omitted from these embodiments. In these embodiments, the sharp distal end of trocar 812 is entirely within through-bore 116 while in the initial position, prior to cannula deployment, to prevent accidental contact by the user. In addition, with cannula 600 in this lower initial position, cannula inserter 800 may be modified to not extend as far above cartridge 100 as in FIG. 10 (see, for instance, FIG. 17), while retaining the above-described or similar components to similarly insert cannula 600 into operating position, as described below. Thus, these embodiments may remove the need for plug 110 while making baseplate assembly 300 more compact and retaining all of its other capabilities.

Figure 11:
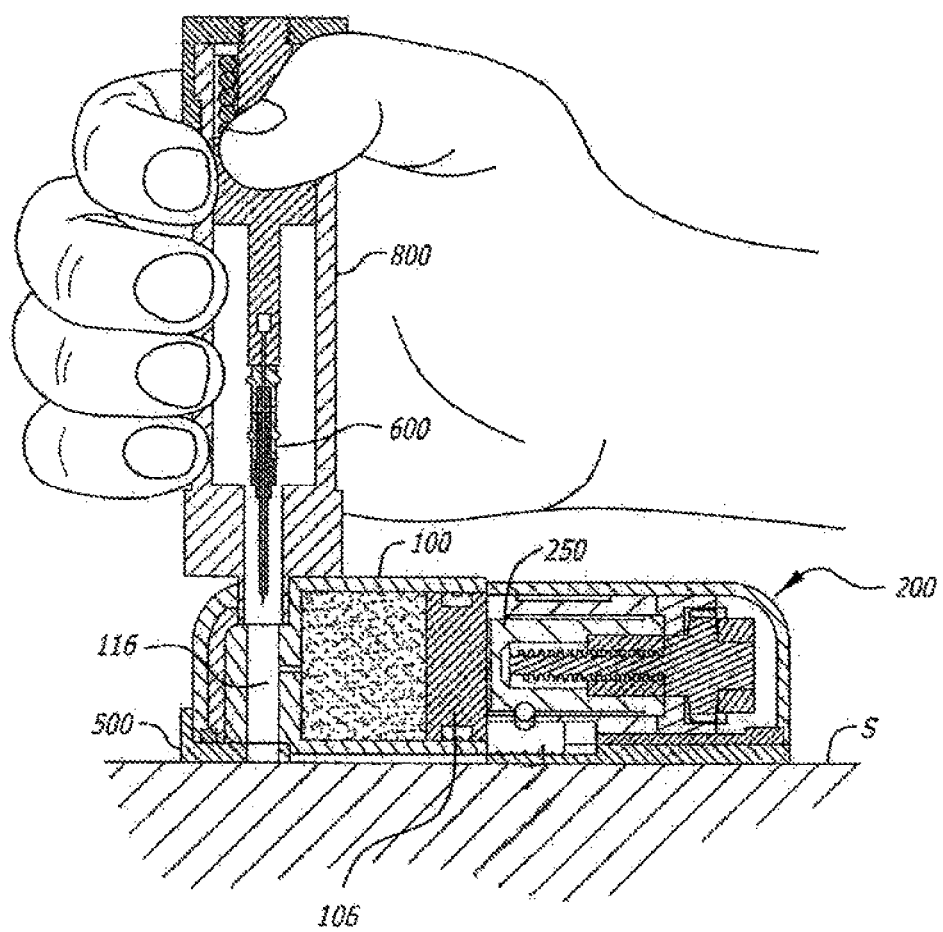
FIG. 11 is a section view showing the system illustrated in FIG. 10 on the cleaned skin prior to cannula insertion.
Figure 12:
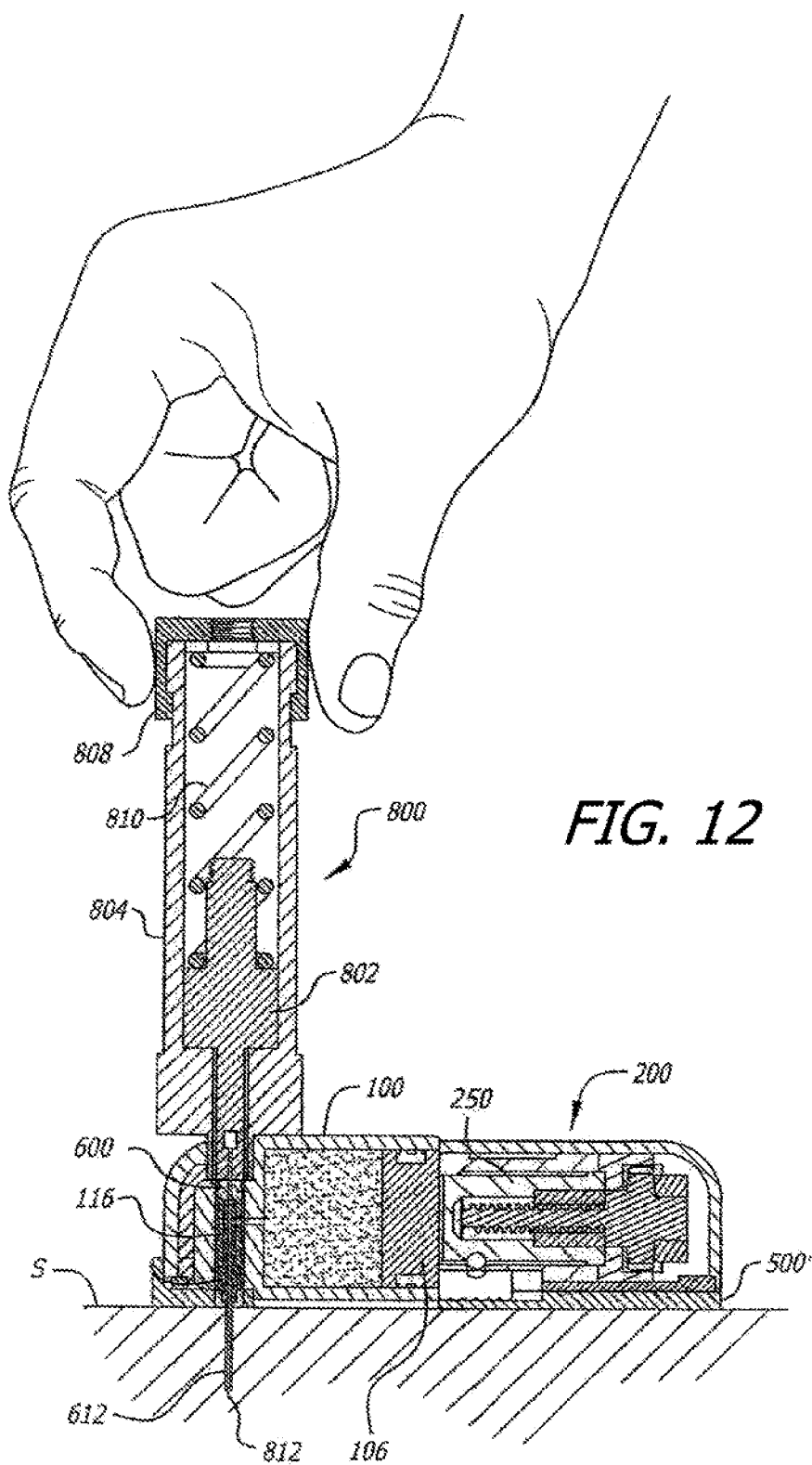
FIG. 12 is a section view showing the system illustrated in FIG. 11 after cannula insertion.
Figure 13:
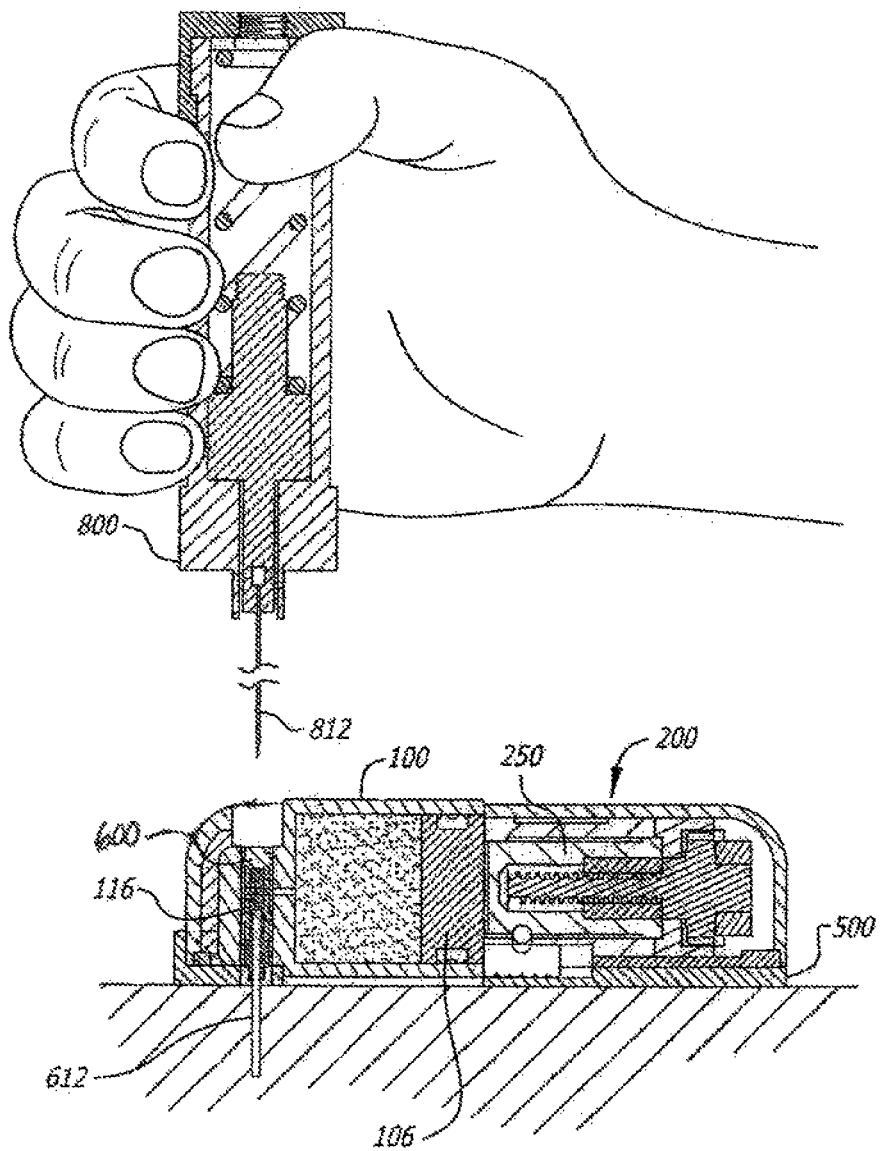
FIG. 13 is a section view showing the system illustrated in FIG. 12 on the skin with the cannula inserted and the inserter being removed.

Turning to FIG. 11, the unit consisting of the pump assembly 200, baseplate assembly 300 (including cartridge 100, baseplate 500, energy supply 400, cannula 600, and inserter 800) may be adhered to the skin surface S (Step S118). The inserter actuator 806 may then be actuated (FIG. 12) such as by pressing or by rotating a trigger 808, thereby allowing spring 810 to drive movable member 802 towards the patient (Step S119). At the end of the movable member stroke, the proximal portion of cannula 600 will be properly seated in the cartridge through-bore 116, and the distal end of cannula 600 will be subcutaneously deployed. The inserter 800 may then be removed (FIG. 13, Step S120).

In some implementations, the pump assembly may be provided with structure (not shown) that performs the function of determining whether or not the cannula is properly inserted (Step S121). If the cannula is not properly inserted, an error message will be provided to the user (Step S122).

Figure 14:
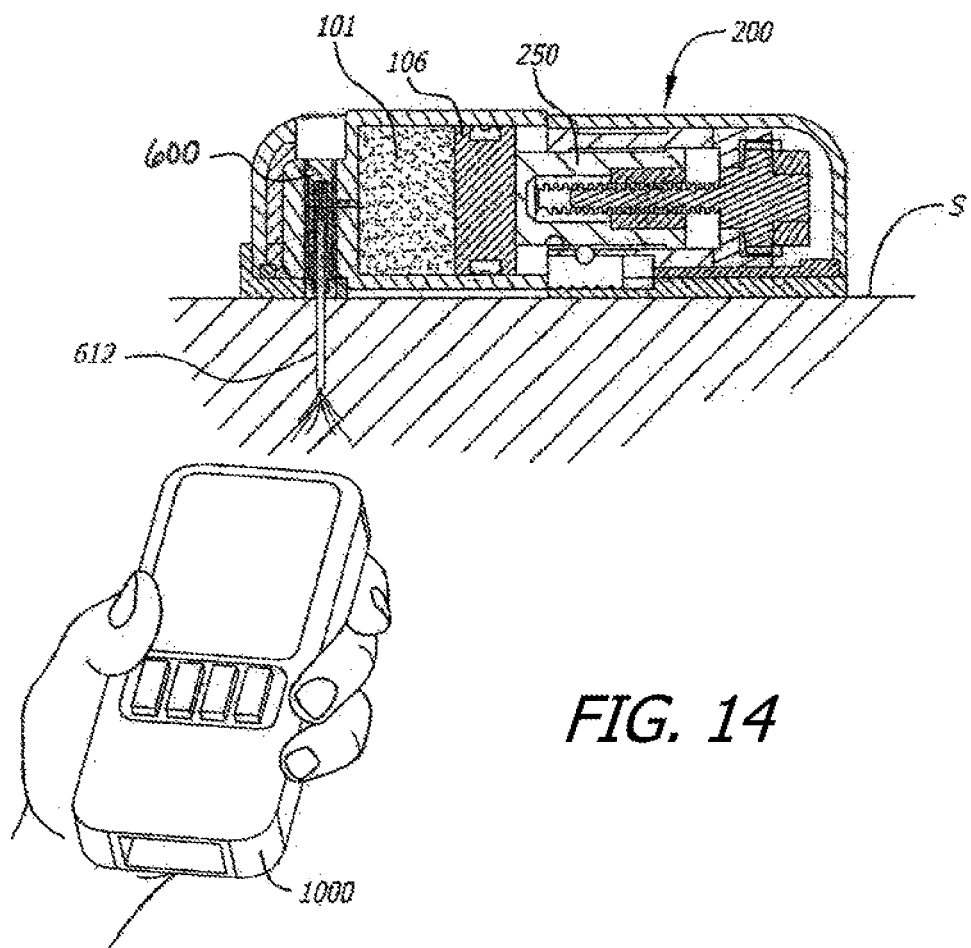
FIG. 14 is a section view showing the system illustrated in FIG. 13 dispensing medicament by way of the cannula.

Finally, as shown in FIG. 14, the remote control 1000 may be used to initiate a particular medicament delivery operation (Step S123). The delivery operation may follow a predetermined delivery profile (e.g. a particular basal rate, a series of time-spaced bolus deliveries, or some combination thereof) that is equated to motor rotations, at particular rates and times, required to deliver medicament in accordance with the profile. The profile may be input by the user with the remote control 1000 and stored by the pump assembly controller. For example, the remote control may store a number of different delivery profiles and bolus deliveries from which the patient can choose. Such profiles may correspond to, for example and depending on the medicament, days where vigorous exercise is expected, days where it is not, incidences of increased pain, etc. Alternatively, or in addition, the profile stored in the pump assembly controller may be set by a clinician's programming unit. In such a case, a remote control may not be needed to initiate, e.g., basal delivery.

The discussion above is also applicable to use of the "pocket pump" system 11. Minor variations in the above-described procedure include, for example, use of baseplate assembly 301 with baseplate 501, deploying the infusion set 503 instead of a cannula, and priming of the infusion set tube.

Another exemplary ambulatory infusion system is generally represented by reference numeral 10' in FIG. 17. The exemplary infusion system 10' is essentially identical to infusion system 10 and similar elements are represented by similar reference numerals. To that end, the pump assembly 200' includes a housing 202', with an inserter opening 224' and cartridge opening 226', and the other internal components described above. The baseplate assembly 300' includes a baseplate 500', an energy supply 400', a medicament cartridge 100' (with a manifold) and an inserter 800' (with a cannula) that are attached to one another in the manner shown. The inserter opening 224' is configured to permit passage of the inserter 800' when the pump assembly 200' is placed over baseplate assembly 300'. After the pump assembly 200' and cartridge assembly 300' are secured to one another, the cannula may be deployed and the inserter 800' removed from the baseplate assembly 300'.

Various methodologies are presented here in the context of the exemplary structures described in the preceding sections, and illustrated in FIGS. 1-17, for the purpose of explanation only. Although the present methodologies may employ the structures described above, they are not limited thereto. Additionally, the alarms, reports and other notifications associated with the methodologies described below may be provided in audible, visible and/or tactile form. A pump assembly may provide audible, visible and/or tactile notifications. A remote control may also provide audible, visible and/or tactile notifications as an alternative to, or in addition to, any notifications provided by a pump assembly. Additionally, embodiments of the present inventions may incorporate any one, combinations of less than all, or all of the methodologies or devices referenced above.

Although the inventions disclosed herein have been described in terms of the preferred embodiments above, numerous modifications and/or additions to the above-described preferred embodiments would be readily apparent to one skilled in the art. It is intended that the scope of the present inventions extends to all such modifications and/or additions and that the scope of the present inventions is limited solely by the claims set forth below or later added.

Finally, with respect to terminology that may be used herein, whether in the description or the claims, the following should be noted. The terms "comprising," "including," "carrying," "having," "containing," "involving," and the like are open-ended and mean "including but not limited to." Ordinal terms such as "first", "second", "third", do not, in and of themselves, connote any priority, precedence, or order of one element over another or temporal order in which steps of a method are performed. Instead, such terms are merely labels to distinguish one element having a certain name from another element having a same name (but for the ordinal term) to distinguish the elements. "And/or" means that the listed items are alternatives, but the alternatives also include any combination of the listed items. The terms "approximately," "about," "substantially" and "generally" allow for a certain amount of variation from any exact dimensions, measurements, and arrangements, and should be understood within the context of the description and operation of the invention as disclosed herein. Terms such as "top," "bottom," "above," and "below" are terms of convenience that denote the spatial relationships of parts relative to each other rather than to any specific spatial or gravitational orientation. Thus, the terms are intended to encompass an assembly of component parts regardless of whether the assembly is oriented in the particular orientation shown in the drawings and described in the specification, upside down from that orientation, or any other rotational variation therefrom.

We claim:

1. An infusion pump system, comprising:
   a baseplate assembly comprising:
   a baseplate;
   a medicament cartridge on the baseplate defining a reservoir; and
   a baseplate energy supply on the baseplate, the baseplate energy supply comprising a housing, an electrical energy storage device within the housing, and a pair of flexible electrical contacts respectively connected to an anode and a cathode of the electrical energy storage device, the baseplate energy supply configured to transfer energy to a replenishable energy supply of a reusable pump assembly when the baseplate assembly is coupled to the reusable pump assembly, the baseplate assembly being a disposable baseplate assembly;
   a cannula; and
   a cannula inserter.

2. The infusion pump system as claimed in claim 1, wherein the cannula is located at least partially within the cannula inserter; and the cannula inserter is removably secured to the medicament cartridge.

3. The infusion pump system as claimed in claim 1, further comprising:
   a manifold;
   wherein the cannula is located at least partially within the cannula inserter, and the cannula inserter is secured to the manifold.

4. The infusion pump system as claimed in claim 3, wherein the manifold is attached to the medicament cartridge.

5. The infusion pump system as claimed in claim 1, further comprising a plug configured to seal the medicament cartridge during a period of non-use.

6. The infusion pump system as claimed in claim 1, wherein the baseplate comprises a pair of opposing connectors and a hook.

7. The infusion pump system as claimed in claim 6, wherein the pair of opposing connectors and the hook are configured to attach the baseplate assembly to the reusable pump assembly.

8. The infusion pump system as claimed in claim 1, wherein the pair of flexible electrical contacts is positioned to engage a plurality of receiving area contacts on a receiving area of the reusable pump assembly when the baseplate assembly is attached to the reusable pump assembly.

9. The infusion pump system as claimed in claim 1, further comprising a seal that extends around a base of the housing.

10. The infusion pump system as claimed in claim 9, wherein the seal is configured to engage a side wall of the receiving area of the reusable pump assembly when the baseplate assembly is attached to the reusable pump assembly.

11. A baseplate assembly comprising:
    a baseplate that is separable from a pump assembly comprising a rechargeable battery; and
    a battery carried on the baseplate, the battery comprising a housing, an electrical energy storage device within the housing, and a pair of flexible electrical contacts respectively connected to an anode and a cathode of the electrical energy storage device, the battery being configured to recharge the rechargeable battery when the baseplate assembly is coupled to the pump assembly.

12. A baseplate assembly, comprising:
    a baseplate that is separable from a pump assembly comprising a replenishable energy supply; and
    a baseplate energy supply on the baseplate, the baseplate energy supply comprising a housing, an electrical energy storage device within the housing, and a pair of flexible electrical contacts respectively connected to an anode and a cathode of the electrical energy storage device, the baseplate energy supply being configured to transfer energy to the replenishable energy supply of the pump assembly when the baseplate assembly is coupled to the pump assembly.

13. The baseplate assembly as claimed in claim 12, wherein the pair of flexible electrical contacts is positioned to engage a plurality of receiving area contacts on a receiving area of a pump assembly when the baseplate assembly is attached to the pump assembly.

14. The baseplate assembly as claimed in claim 12, further comprising a seal that extends around a base of the housing.

15. The baseplate assembly as claimed in claim 14, wherein the seal is configured to engage a side wall of the receiving area of the pump assembly when the baseplate assembly is attached to the pump assembly.

\* \* \* \* \*